(12) United States Patent
Panarese et al.

(10) Patent No.: US 11,993,600 B2
(45) Date of Patent: May 28, 2024

(54) SATURATED SPIROCYCLICS AS ANTIVIRAL AGENTS

(71) Applicant: ENANTA PHARMACEUTICALS, INC., Watertown, MA (US)

(72) Inventors: Joseph D. Panarese, Newton, MA (US); Samuel Bartlett, Brighton, MA (US); Yat Sun Or, Waltham, MA (US)

(73) Assignee: Enanta Pharmaceuticals, Inc., Watertown, MA (US)

(*) Notice: Subject to any disclaimer, the term of this patent is extended or adjusted under 35 U.S.C. 154(b) by 21 days.

(21) Appl. No.: 18/075,567

(22) Filed: Dec. 6, 2022

(65) Prior Publication Data

US 2023/0174531 A1    Jun. 8, 2023

Related U.S. Application Data

(60) Provisional application No. 63/287,189, filed on Dec. 8, 2021.

(51) Int. Cl.
    C07D 471/10    (2006.01)
    A61P 31/14     (2006.01)
    C07D 487/10    (2006.01)

(52) U.S. Cl.
    CPC ........... C07D 471/10 (2013.01); A61P 31/14 (2018.01); C07D 487/10 (2013.01)

(58) Field of Classification Search
    CPC .. C07D 471/10; C07D 487/10; C07D 471/04; C07D 487/04; C07D 519/00; A61P 31/14
    See application file for complete search history.

(56) References Cited

U.S. PATENT DOCUMENTS

| | | | |
|---|---|---|---|
| 8,088,815 B2 | 1/2012 | Bartkovitz et al. | |
| 8,222,288 B2 | 7/2012 | Wang et al. | |
| 8,222,425 B2 | 7/2012 | Britt et al. | |
| 8,372,802 B2 | 2/2013 | Gai et al. | |
| 8,546,416 B2 * | 10/2013 | Ambarkhane | A61P 1/08 546/15 |
| 9,290,757 B2 | 3/2016 | Madison | |
| 9,309,284 B2 | 4/2016 | Chang et al. | |
| 9,428,739 B2 | 8/2016 | Colt et al. | |
| 9,474,759 B2 | 10/2016 | Chang et al. | |
| 9,591,858 B2 | 3/2017 | Valles et al. | |
| 9,828,342 B2 | 11/2017 | Horne et al. | |
| 9,975,885 B2 | 5/2018 | St John et al. | |
| 10,017,463 B2 | 7/2018 | Hedstrom et al. | |
| 10,130,701 B2 | 11/2018 | Bickerton et al. | |
| 10,590,084 B2 | 3/2020 | Buckman et al. | |
| 10,934,261 B2 | 3/2021 | Buckman et al. | |
| 10,959,969 B1 | 3/2021 | Johnson | |
| 11,013,779 B2 | 5/2021 | Chang et al. | |
| 11,021,513 B2 | 6/2021 | Schinazi et al. | |
| 11,033,600 B2 | 6/2021 | Chang et al. | |
| 11,045,546 B1 | 6/2021 | Kelly et al. | |
| 11,058,763 B2 | 7/2021 | Zhang et al. | |
| 11,058,779 B2 | 7/2021 | Lu et al. | |
| 11,124,497 B1 | 9/2021 | Arnold et al. | |
| 11,174,231 B1 | 11/2021 | Arnold et al. | |
| 11,207,370 B2 | 12/2021 | Schinazi et al. | |
| 11,319,325 B1 | 5/2022 | Zhang et al. | |
| 11,325,916 B1 | 5/2022 | Shen et al. | |
| 11,339,170 B1 | 5/2022 | Gao et al. | |
| 11,352,363 B1 | 6/2022 | Wang et al. | |
| 11,358,953 B2 | 6/2022 | Panarese et al. | |
| 11,384,090 B2 | 7/2022 | Wang et al. | |
| 2005/0143320 A1 | 6/2005 | Yang et al. | |
| 2006/0014821 A1 | 1/2006 | He et al. | |

(Continued)

FOREIGN PATENT DOCUMENTS

| | | |
|---|---|---|
| CN | 114057624 A | 2/2022 |
| CN | 115894504 A | 4/2023 |

(Continued)

OTHER PUBLICATIONS

Panarese, Joseph D et al., U.S. Appl. No. 18/102,850, filed Jan. 30, 2023.
Wang, Guoqiang et al., U.S. Appl. No. 17/983,474, filed Nov. 9, 2022.
Pubchem, SID 326247498, deposited Jan. 25, 2017.
Bafna, K., et al., "Structural Similarity of SARS-CoV2 Mpro and HCV NS3/4A Proteases Suggests New Approaches for Identifying Existing Drugs Useful as COVID-19 Therapeutics", ChemRxiv online at DOI: 10.26434/chem rxiv.12153615. v1.
Dai, W., et al., "Structure-based design of antiviral drug candidates targeting the SARS-CoV-2 main protease", Science, 368(6497), 1331-1334.

(Continued)

*Primary Examiner* — Jeffrey S Lundgren
*Assistant Examiner* — Alexander K. Showalter
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, thereof:

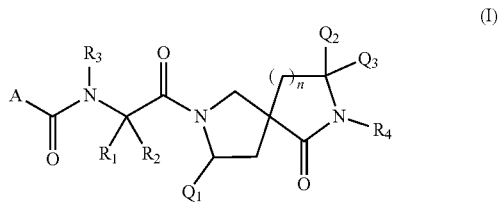

(I)

which inhibit coronavirus replication activity. The invention further relates to pharmaceutical compositions comprising a compound of Formula (I) or a pharmaceutically acceptable salt thereof, and methods of treating or preventing a coronavirus infection in a subject in need thereof, comprising administering to the subject a therapeutically effective amount of a compound of Formula (I) or a pharmaceutically acceptable salt thereof.

16 Claims, No Drawings

(56) References Cited

U.S. PATENT DOCUMENTS

| | | |
|---|---|---|
| 2008/0125430 A1 | 5/2008 | Wang et al. |
| 2009/0137818 A1 | 5/2009 | Hilgenfeld et al. |
| 2010/0272681 A1 | 10/2010 | Farmer et al. |
| 2010/0317661 A1 | 12/2010 | Wang et al. |
| 2013/0072500 A1 | 3/2013 | Banka et al. |
| 2013/0072686 A1 | 3/2013 | Cadieux et al. |
| 2014/0148494 A1 | 5/2014 | Wang et al. |
| 2014/0243341 A1 | 8/2014 | Chang et al. |
| 2014/0378680 A1 | 12/2014 | Wang et al. |
| 2015/0133368 A1 | 5/2015 | Chang et al. |
| 2015/0336928 A1 | 11/2015 | Fang et al. |
| 2016/0014821 A1 | 1/2016 | Toebes |
| 2017/0044183 A1 | 2/2017 | Lim et al. |
| 2018/0099981 A1 | 4/2018 | Estrada et al. |
| 2019/0161472 A1 | 5/2019 | Ombrato et al. |
| 2020/0230198 A1 | 7/2020 | Chang et al. |
| 2021/0355111 A1 | 11/2021 | Arnold et al. |
| 2022/0033383 A1 | 2/2022 | Panarese et al. |
| 2022/0041652 A1 | 2/2022 | Panarese et al. |
| 2022/0048944 A1 | 2/2022 | Panarese et al. |
| 2022/0162216 A1 | 5/2022 | Wang et al. |
| 2022/0162231 A1 | 5/2022 | Wang et al. |
| 2022/0380377 A1 | 12/2022 | Zhang et al. |
| 2022/0402926 A1 | 12/2022 | Zhang et al. |
| 2023/0103494 A1 | 4/2023 | Wang et al. |
| 2023/0115107 A1 | 4/2023 | Gao et al. |
| 2023/0122228 A1 | 4/2023 | Shen et al. |
| 2023/0151019 A1 | 5/2023 | Cao et al. |
| 2023/0159545 A1 | 5/2023 | Panarese et al. |
| 2023/0159546 A1 | 5/2023 | Kass et al. |
| 2023/0174531 A1 | 6/2023 | Panarese et al. |
| 2023/0203048 A1 | 6/2023 | Wang et al. |

FOREIGN PATENT DOCUMENTS

| | | |
|---|---|---|
| GB | 2595975 A | 12/2021 |
| WO | 0059929 A1 | 10/2000 |
| WO | 0208244 A2 | 1/2002 |
| WO | 2004101742 A3 | 6/2005 |
| WO | 2005113580 A1 | 12/2005 |
| WO | 2006061714 A2 | 6/2006 |
| WO | 2007038138 A2 | 4/2007 |
| WO | 2008144507 A2 | 11/2008 |
| WO | 2012099454 A1 | 7/2012 |
| WO | 2013049382 A3 | 5/2013 |
| WO | 2013166319 A1 | 11/2013 |
| WO | 2017222935 A1 | 12/2017 |
| WO | 2018023054 A1 | 2/2018 |
| WO | 2018042343 A2 | 3/2018 |
| WO | 2019086141 A1 | 5/2019 |
| WO | 2019086142 A1 | 5/2019 |
| WO | 2020081636 A1 | 4/2020 |
| WO | 2021205296 A1 | 10/2021 |
| WO | 2021206876 A1 | 10/2021 |
| WO | 2021206877 A1 | 10/2021 |
| WO | 2021207409 A2 | 10/2021 |
| WO | 2021226546 A1 | 11/2021 |
| WO | 2021250648 A1 | 12/2021 |
| WO | 2021252491 A1 | 12/2021 |
| WO | 2021252644 A1 | 12/2021 |
| WO | 2022013684 A1 | 1/2022 |
| WO | 2022020242 A1 | 1/2022 |
| WO | 2022020711 A1 | 1/2022 |
| WO | 2022109363 A1 | 5/2022 |

OTHER PUBLICATIONS

Marti, C., "Novel Approach to Spiro-Pyrrolidine-Oxindoles and its Application to the Synthesis of (+−)-Horsfiline and (−)-Spirotryprostatin", ETH Library, Doctoral Thesis, 1-2, 23-25.

Vandyck, K., et al., "Considerations for the discovery and development of 3-chymotrypsin-like cysteine protease inhibitors targeting SARS-CoV-2 infection", Current opinion in virology, 49, 36-40.

Ziarani, G., et al., "Synthesis of Spiro-Fused Heterocyclic Scaffolds Through Multicomponent Reactions Involving Isatin", ARKIVOC, 2016 (i) , 1, 14-16.

PubChem, SID 160923150, deposited Mar. 4, 2013.

PubChem, SID 267351747, deposited Dec. 11, 2015.

PubChem, SID 367622864, May 25, 2018.

Anonymous, "Nirmatrelvir", Cortellis Database, Retrieved from the Internet: URL:https://www.cortellis.com/drugdiscover /entity/drug/1126756/product?ent=qR5ruNw5&updateHistoryPage=5&orderBy=_score:desc, Nov. 8, 2022, 3 pgs.

Anonymous, "Pfizer Initiates Phase 1 Study of Novel Oral Antiviral Therapeutic Agent Against SARS-CoV-2 Science Products Stories Newsroom About", Retrieved from the Internet: URL:https://www.pfizer.com/news/press-release/press-release-detail/pfizer-initiatesphase-1-study-novel-oral-antiviral [retrieved on Nov. 11, 2022], 9 pgs.

Chia, C.S. B. "Novel Coronavirus Main Protease Di- and Tripeptide Inhibitors for Treating COVID-19", ACS Med. Chem. Lett., 13(9), URL:https://pubs.acs.org/doi/pdf/10.1021/acsmedchemlett.2c00332, Aug. 8, 2022, 1388-1389.

Efremov, I. et al., "Discovery and Optimization of a Novel Spiropyrrolidine Inhibitor of B-Secretase (BACE1) through Fragment-Based Drug Design", J. Med. Chem., vol. 55, Apr. 2, 2012, 9069-9088.

Halford, B., "Pfizer unveils its oral SARS-00V-2 inhibitor—The antiviral candidate is the first orally administered compound to enter clinical trials that targets the virus's main protease", Chem. & Eng. News, online at https://cen.acs.org/acs-news/acs-meeting-news/Pfizer-unveils-oral-SARS-CoV/99/i13, (a version appeared in 99(13)), Apr. 7, 2021, 2 pgs.

Halford, B., "Pfizer's novel COVID-19 antiviral heads to clinical trials—The small molecule targets coronavirus 3CL protease and is active against multiple coronaviruses in cell studies", Chem. & Eng. News, online at https://cen.acs.org/pharmaceuticals/drug-discovery/Pfizers-novel-COVID-19-antiviral/98/web/2020/09, Sep. 17, 2020, 2 pgs.

Konno, S. et al., "3CL Protease Inhibitors with an Electrophilic Arylketone Moiety as Anti-SARS-CoV-2 Agents", J. Medicinal Chemistry, https://doi.org/10.1021/acs.jmedchem.1c00665, Jul. 27, 2021, pp. 1-14.

Lee., C. et al., "Structural Basis of Inhibition Specificities of 3C and 3C-like Proteases by Zinc-coordinating and Peptidomimetic Compounds", J. Biological Chem., 284(12), Mar. 20, 2009, 7646-7655.

Mandadapu, S. et al., "Macrocyclic Inhibitors of 3c and 3C-Like Proteases of Picornavirus, Norovirus, and Coronavirus", Bioorg. & Med. Chem. Lett., 23, http:lfdx.doi.org/10.1016/j.bmcl.2013.05.021, May 16, 2013, 3709-3712.

Owen, D., "Oral inhibitors of the 1-12 SARS-CoV-2 main protease for the treatment of COVID-19", 261st Am. Chem. Soc. (ACS) Natl Meet, Apr. 16, 2021, 1 pg.

Thanigaimalai, P. et al., "Design, synthesis, and biological evaluation of novel dipeptide-type SARS-CoV 3CL protease inhibitors: Structure-activity relationship study", Euro J. Med. Chem., 65, DOI: 10.1016/J.EJMECH.2013.05.005, May 20, 2013, 436-447.

Wang, Y. et al., "Inhibition of Enterovirus 71 Replication by an a-Hydroxy-Nitrile Derivative NK-1.9k", Antiviral Res., 141, Jan. 5, 2017, 91-100.

Xu, J. et al., "Green Oxidation of Indoles Using Halide Catalysis", Nature Communications, 10:4754, https://doi.org/10.1038/s41467-019-12768-4, Oct. 18, 2019, 1-11.

Yang, S. et al., "Synthesis, Crystal Structure, Structure-Activity Relationships, and Antiviral Activity of a Potent SARS Coronavirus 3CL Protease Inhibitor", J. Med. Chem., 49, Jul. 14, 2006, 4971-4980.

Zhang, L. et al., "A-Ketoamides as Broad-Spectrum Inhibitors of Coronavirus and Enterovirus Replication: Structue-Based Design, Synthesis, and Activity Assessment", J. Med. Chem., 63, https://dx.doi.org/10.1021/acs,jmedchem.9b01828, 2020, 4562-4578.

Zhou, L. et al., "An Overview of Spirooxindole as a Promising Scaffold for Novel Drug Discovery", Expert Opinion on Drug Discovery, 15(5), Feb. 2020, 603-625.

"1-(2-oxospiro[1H-indole-3,3'-pyrrolidine]-1'-yl)-4-pyridin-2-ylbutane-1,4-dione", Pubchem CID 145894940. Create Date: Feb. 12, 2020. Date Accessed: Jun. 9, 2023, 2 pgs.

(56) References Cited

OTHER PUBLICATIONS

Baker, J. D, et al., "A drug repurposing screen identifies hepatitis C antivirals as inhibitors of the SARS-CoV-2 main 1 protease", BioRxiv. Preprint. avail at https://doi.org/10.1101/2020.07.10.197889, Jul. 10, 2020.

Zhai, Y., et al., "Cyanohydrin as an Anchoring Group for Potent and Selective Inhibitors of Enterovirus 71 3C Protease", J. Med. Chem., 58, 9414-9420.

Chuck, C-P et al., "Design, synthesis and crystallographic analysis of nitrile-based broad-spectrum peptidomimetic inhibitors for coronavirus 3C-like proteases", Euro. J. Med. Chem., 59, https://doi.org/10.1016/j.ejmech.2012.10.053, Jan. 2013, 1-6.

Kelemen, A. et al., "Spiro[pyrrolidine-3,3'-oxindoles] and Their Indoline Analogues as New 5-HT6 Receptor Chemotypes", Molecules, vol. 22, DOI: 10.3390/molecules22122221, Dec. 14, 2017, 1-25.

\* cited by examiner

SATURATED SPIROCYCLICS AS ANTIVIRAL AGENTS

RELATED APPLICATION

This application claims the benefit of U.S. Provisional Application No. 63/287,189, filed on Dec. 8, 2021. The entire teachings of the above application are incorporated herein by reference.

TECHNICAL FIELD

The invention relates to compounds and methods of inhibiting coronavirus replication activity by targeting the 3C-Like protease (sometimes referred to as "3CLpro", "Main protease", or "Mpro") with a therapeutically effective amount of a 3C-Like protease inhibitor. The invention further relates to pharmaceutical compositions containing the coronavirus 3C-Like protease inhibitor in a mammal by administering effective amounts of such coronavirus 3C-Like protease inhibitor.

BACKGROUND OF THE INVENTION

Coronaviruses are family of single-stranded, positive-strand RNA viruses with viral envelopes, classified within the Nidovirales order. The coronavirus family comprises pathogens of many animal species, including humans, horses, cattle, pigs, birds, cats and monkeys, and have been known for more than 60 years. The isolation of the prototype murine coronavirus strain JHM, for example, was reported in 1949. Coronaviruses are common viruses that generally cause mild to moderate upper-respiratory tract illnesses in humans and are named for the crown-like spikes on their envelope surface. There are four major sub-groups known as alpha, beta, gamma and delta coronaviruses, with the first coronaviruses identified in the mid-1960s. The coronaviruses known to infect humans include alpha coronaviruses 229E and NL63; and beta coronaviruses OC43, HKU1, SARS-CoV (the coronavirus that causes severe acute respiratory syndrome, or SARS), and MERS-CoV (the coronavirus that causes Middle East Respiratory Syndrome, or MERS). People are commonly infected with human coronaviruses 229E, NL63, 0C43 and HKU1, and symptoms usually include mild to moderate upper-respiratory tract illnesses of short duration, such as runny nose, cough, sore throat, and fever. Occasionally human coronaviruses result in lower-respiratory tract illnesses, such as pneumonia, although this is more common in people with cardiopulmonary disease or compromised immune systems, or in the elderly. Transmission of the common human coronaviruses is not fully understood. However, it is likely that human coronaviruses spread from an infected person to others through the air by coughing and sneezing, and through close personal contact, such as touching or shaking hands. These viruses may also spread by touching contaminated objects or surfaces then touching the mouth, nose, or eyes.

Coronaviruses are enveloped, positive-sense, single-stranded RNA viruses. The genomic RNA of CoVs has a 5'-cap structure and 3'-poly-A tail and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, only one has been approved to date as a coronavirus therapy. (Refer to WO 2004101742 A2, US 2005/0143320 A1, US 2006/0014821 A1, US 2009/0137818 A1, WO 2013/049382 A2, WO 2013/166319 A1, WO2018042343 A1, WO2018023054 A1, WO2005113580 A1, WO2006061714 A1, WO2021/205296 A1, WO2021/206876 A1, WO2021/206877 A1, WO2021/207409 A2, WO2021/176369, WO2021/191827, WO2021/212039, WO 2021/252491, WO 2022/020242, WO 2022/020711, WO2022/036018, WO 2022/109360, WO 2022/109363, U.S. Pat. No. 11,124,497 B1, U.S. Pat. No. 11,174,231 B1 and U.S. Pat. No. 11,351,149 B1).

More effective therapies for coronavirus infections are needed due to this high unmet clinical need.

SUMMARY OF THE INVENTION

The present invention relates to novel antiviral compounds, pharmaceutical compositions comprising such compounds, as well as methods for treating or preventing viral (particularly coronavirus) infection in a subject in need of such therapy with said compounds. Compounds of the present invention inhibit the protein(s) encoded by a coronavirus or interfere with the life cycle of a coronavirus and are also useful as antiviral agents. In addition, the present invention provides processes for the preparation of said compounds.

In one embodiment, the present invention provides compounds represented by Formula (I), and pharmaceutically acceptable salts, esters, and prodrugs thereof,

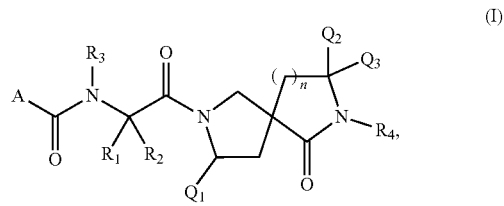

wherein:
A is selected from:
  1) —$R_{11}$;
  2) —$OR_{12}$;
  3) —$NR_{17}R_{18}$; and
  4) —$C(R_{13})(R_{14})NR_{17}R_{18}$;
n is 1, 2, or 3;
$Q_1$ is selected from:
  1) —CN;
  2) —$C(O)R_{15}$;
  3) —$CH(OH)SO_3R_{16}$;
  4) —$C(O)NR_{13}R_{14}$;
  5) —$C(O)C(O)NR_{13}R_{14}$; and
  6) Optionally substituted —$C_2$-$C_8$ alkynyl;

$R_1$, $R_2$, $R_3$, $Q_2$, and $Q_3$ are each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;
alternatively, $R_1$ and $R_2$ are taken together with the carbon atom to which they are attached to form an optionally substituted 3- to 8-membered carbocyclic ring or an optionally substituted 3- to 8-membered heterocyclic ring;
alternatively, $Q_2$ and $Q_3$ are taken together with the carbon atom to which they are attached to form an optionally substituted 3- to 8-membered carbocyclic ring or an optionally substituted 3- to 8-membered heterocyclic ring.
$R_4$ is hydrogen, optionally substituted —$C_1$-$C_4$ alkyl, optionally substituted $C_2$-$C_4$-alkenyl, or optionally substituted —$C_3$-$C_6$ cycloalkyl.
$R_{11}$ and $R_{12}$ are each independently selected from:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted 3- to 8-membered heterocycloalkyl;
6) Optionally substituted aryl;
7) Optionally substituted arylalkyl;
8) Optionally substituted heteroaryl; and
9) Optionally substituted heteroarylalkyl;
$R_{13}$, $R_{14}$, and $R_{17}$ are each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;
alternatively, $R_{13}$ and $R_{14}$ are taken together with the nitrogen atom to which they are attached to form an optionally substituted 3- to 8-membered heterocyclic ring;
$R_{15}$ is hydrogen, hydroxy, or optionally substituted —$C_1$-$C_8$ alkyl; and
$R_{16}$ is hydrogen or $Na^+$; and
$R_{18}$ is selected from:
1) —$C(O)R_{11}$;
2) —$C(O)OR_{11}$;
3) —$C(O)NR_{13}R_{14}$;
4) —$S(O)_2R_{11}$;
5) Hydrogen;
6) Optionally substituted —$C_1$-$C_8$ alkyl;
7) Optionally substituted —$C_2$-$C_8$ alkenyl;
8) Optionally substituted —$C_2$-$C_8$ alkynyl;
9) Optionally substituted —$C_3$-$C_8$ cycloalkyl;
10) Optionally substituted 3- to 8-membered heterocycloalkyl;
11) Optionally substituted aryl;
12) Optionally substituted arylalkyl;
13) Optionally substituted heteroaryl; and
14) Optionally substituted heteroarylalkyl.

DETAILED DESCRIPTION OF THE INVENTION

In one embodiment of the present invention is a compound of Formula (I) as described above, or a pharmaceutically acceptable salt thereof.

In one embodiment of the present invention, the compound of Formula (I) is represented by Formula (I-a) or Formula (I-b).

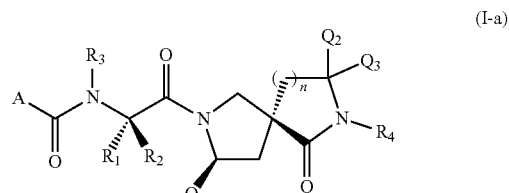

(I-a)

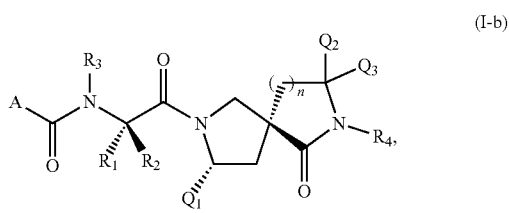

(I-b)

wherein n, A, $Q_1$, $Q_2$, $Q_3$, $R_1$, $R_2$, $R_3$, and $R_4$ are as previously defined.

In a preferred embodiment, the compound of Formula (I) has the stereochemistry shown in Formula (I-a).

In certain embodiments of the compounds of Formula (I), n is 1 or 2.

In certain embodiments of the compounds of Formula (I), $R_1$ is hydrogen, optionally substituted —$C_1$-$C_6$ alkyl; optionally substituted —$C_3$-$C_6$ cycloalkyl; optionally substituted —$C_3$-$C_6$ cycloalkyl-$C_1$-$C_2$-alkyl; optionally substituted aryl; optionally substituted arylalkyl; or optionally substituted heteroarylalkyl.

In certain embodiments of the compounds of Formula (I), $R_1$ is selected from:

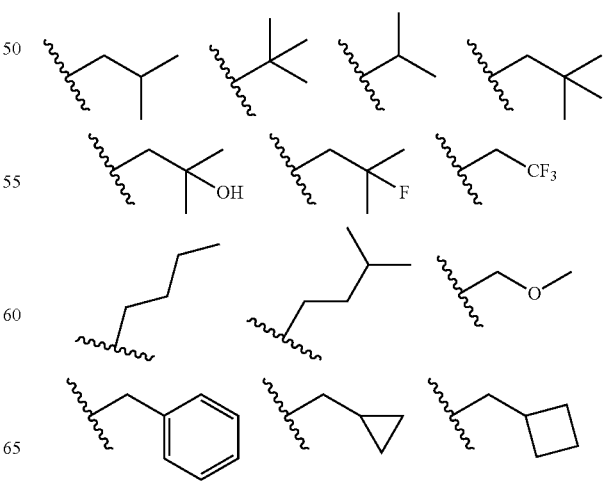

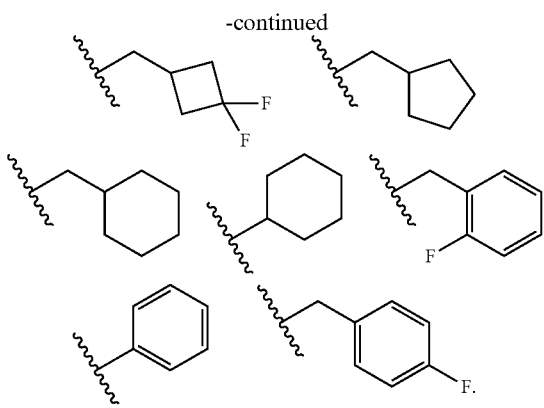

In certain embodiments of the compounds of Formula (I), $R_2$ is hydrogen, optionally substituted —$C_1$-$C_6$ alkyl; optionally substituted —$C_3$-$C_6$ cycloalkyl; optionally substituted aryl; optionally substituted arylalkyl; or optionally substituted heteroarylalkyl.

In certain embodiments of the compounds of Formula (I), $R_3$ is hydrogen or optionally substituted —$C_1$-$C_4$ alkyl; $R_4$ is hydrogen or optionally substituted —$C_1$-$C_4$ alkyl.

In certain embodiments of the compounds of Formula (I), $R_3$ is hydrogen, -Me, -Et, —Pr, -i-Pr, -allyl, —$CF_3$, -$CD_3$ or cyclopropyl.

In certain embodiments of the compounds of Formula (I), $R_4$ is hydrogen, -Me, -Et, —Pr, -i-Pr, -allyl, —$CF_3$ or cyclopropyl.

In certain embodiments of the compounds of Formula (I), $R_2$ is hydrogen; and $R_4$ is hydrogen.

In certain embodiments of the compounds of Formula (I), $Q_1$ is —CN.

In certain embodiments of the compounds of Formula (I), $Q_1$ is —C≡CH.

In certain embodiments of the compounds of Formula (I), $Q_1$ is —C(O)H.

In certain embodiments of the compounds of Formula (I), $Q_1$ is —C(O)C(O)$NR_{13}R_{14}$, wherein $R_{13}$ and $R_{14}$ are previously defined.

In certain embodiments of the compounds of Formula (I), $Q_1$ is selected from the following:

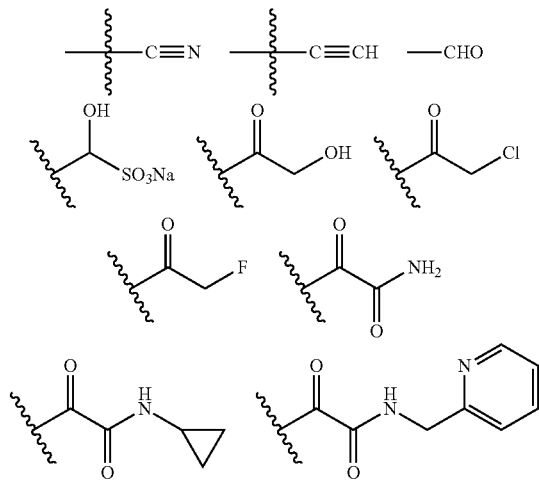

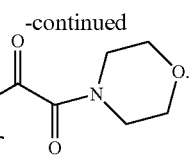

In certain embodiments of the compounds of Formula (I), $Q_2$ is hydrogen, optionally substituted —$C_1$-$C_6$ alkyl; optionally substituted —$C_3$-$C_6$ cycloalkyl; optionally substituted aryl; optionally substituted arylalkyl; or optionally substituted heteroarylalkyl.

In certain embodiments of the compounds of Formula (I), $Q_2$ is hydrogen, -Me, -Et, —Pr, -i-Pr, -allyl, —$CF_3$, -$CD_3$ or cyclopropyl.

In certain embodiments of the compounds of Formula (I), $Q_3$ is hydrogen, optionally substituted —$C_1$-$C_6$ alkyl; optionally substituted —$C_3$-$C_6$ cycloalkyl; optionally substituted aryl; optionally substituted arylalkyl; or optionally substituted heteroarylalkyl.

In certain embodiments of the compounds of Formula (I), $Q_3$ is hydrogen, -Me, -Et, —Pr, -i-Pr, -allyl, —$CF_3$, -$CD_3$ or cyclopropyl.

In certain embodiments of the compounds of Formula (I), $R_2$ is hydrogen; $R_4$ is hydrogen; $Q_1$ is —CN; $Q_2$ is hydrogen; $Q_3$ is hydrogen; $R_3$ is hydrogen, -Me, -Et, —Pr, -i-Pr, -allyl, —$CF_3$, -$CD_3$, or cyclopropyl; and $R_1$ is selected from:

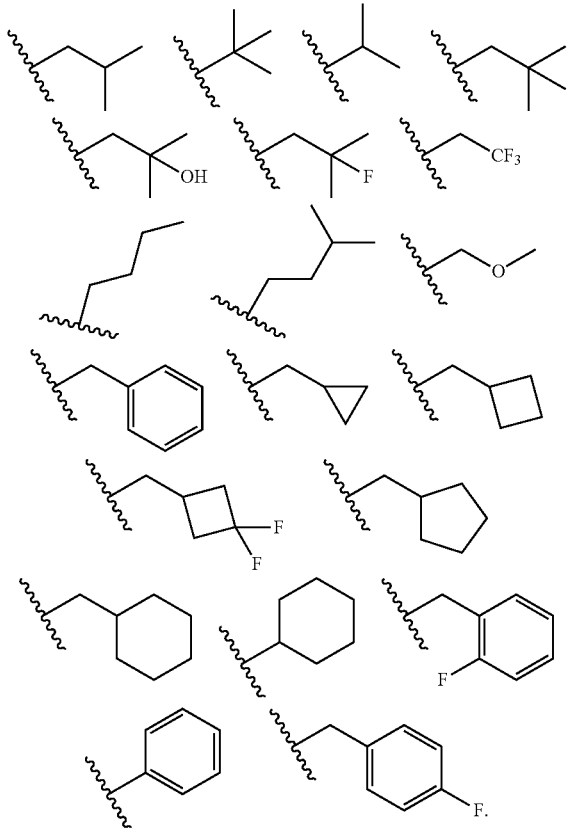

In certain embodiments of the compounds of Formula (I), A is derived from one of the following by removal of a hydrogen atom and is optionally substituted:

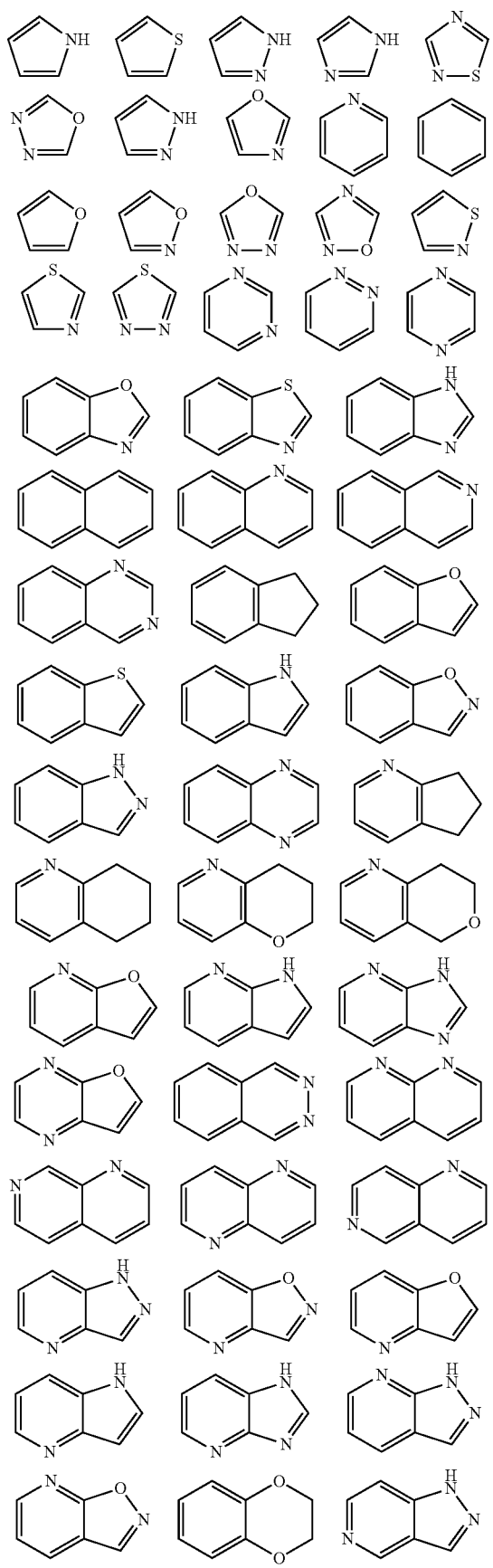
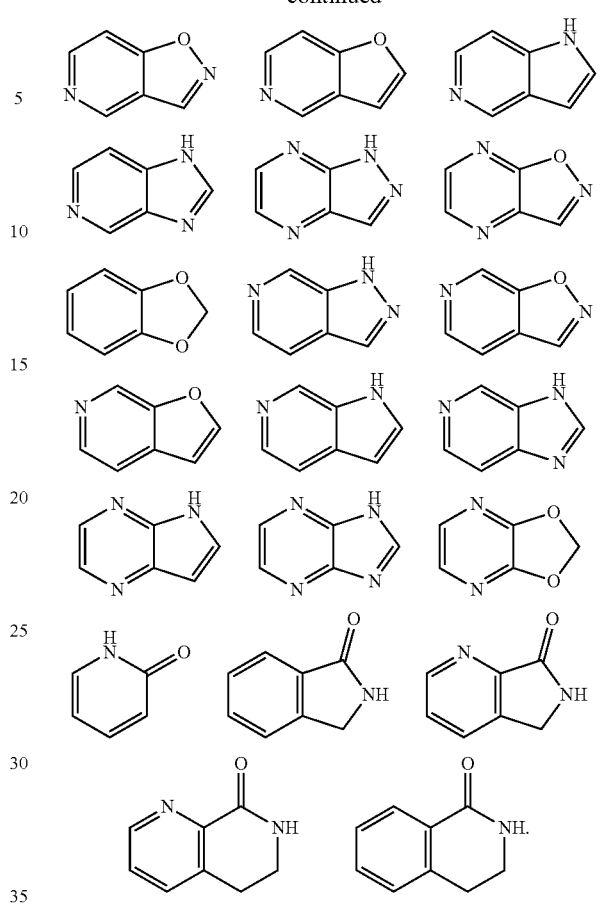
In certain embodiments of the compounds of Formula (I), A is selected from the following groups, and A is optionally substituted:
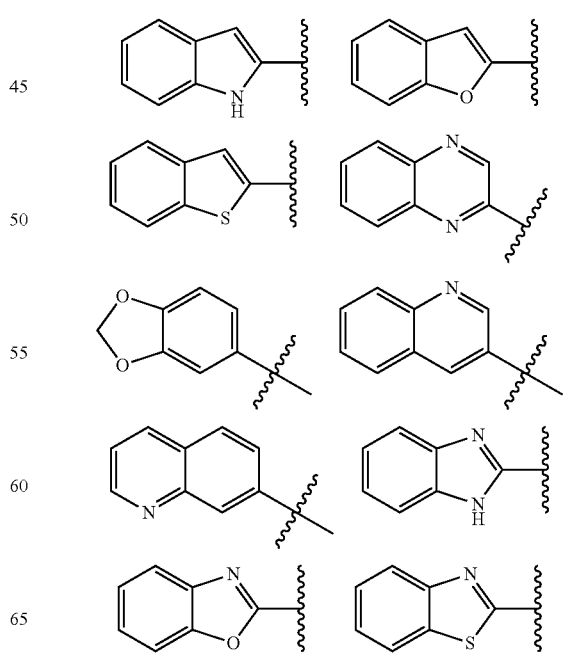

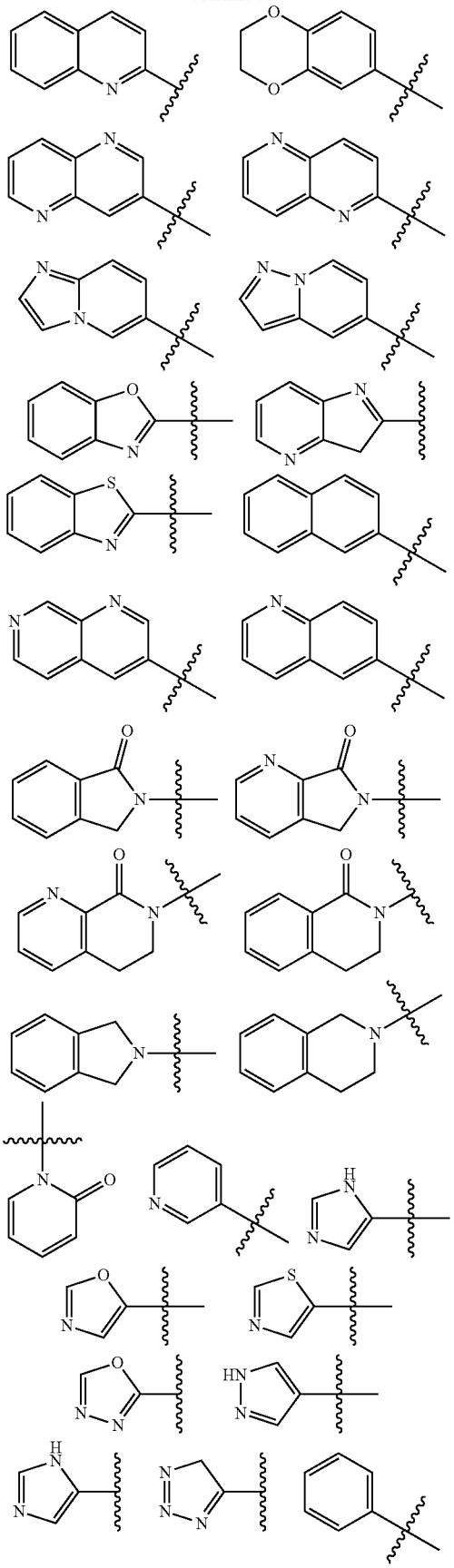
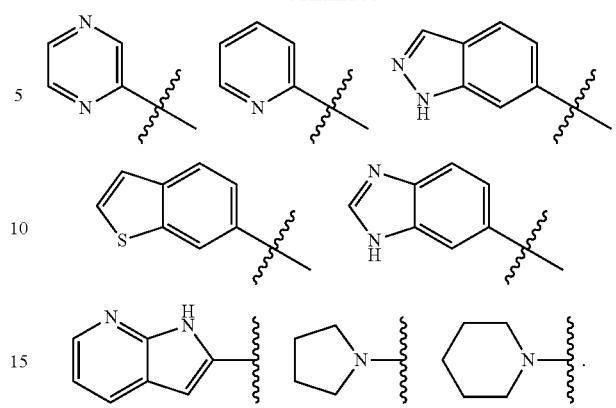

Preferably there are 0, 1, 2 or 3 substituents. Preferably the substituents are independently selected from halogen, optionally substituted —$C_1$-$C_3$ alkoxy, optionally substituted —$C_1$-$C_3$ alkyl, optionally substituted —$C_3$-$C_6$ cycloalkyl, optionally substituted aryl, and optionally substituted heteroaryl.

In certain embodiments of the compounds of Formula (I), A is selected from the following groups, and A is optionally substituted:

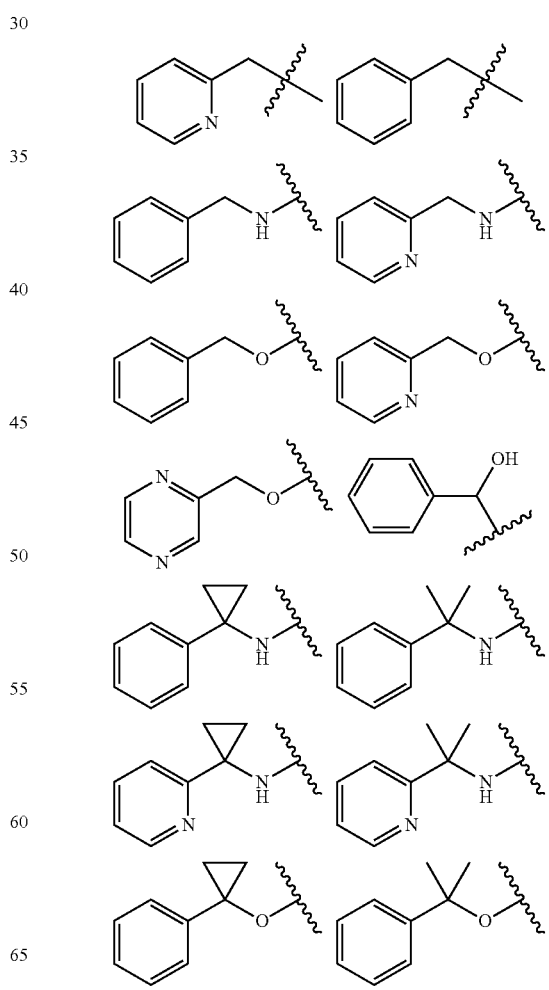

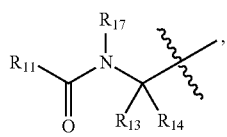

Preferably there are 0, 1, 2 or 3 substituents. Preferably the substituents are independently selected from halogen, CN, NH$_2$, optionally substituted —C$_1$-C$_3$ alkoxy, optionally substituted—C$_1$-C$_3$ alkyl, optionally substituted —C$_3$-C$_6$ cycloalkyl, optionally substituted aryl, and optionally substituted heteroaryl. Preferably the number of substituents is 0 to 3.

In certain embodiments of the compounds of Formula (I), A is

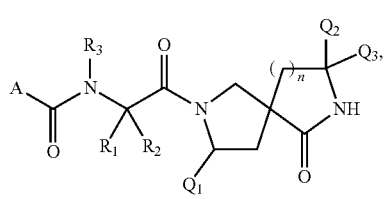

wherein R$_{11}$, R$_{13}$, R$_{14}$, and R$_{17}$ are as previously defined. In certain embodiments, R$_{13}$ and R$_{17}$ are hydrogen and R$_{14}$ is optionally substituted C$_1$-C$_6$-alkyl, preferably optionally substituted t-butyl, and R$_{11}$ is preferably optionally substituted benzyl, optionally substituted C$_1$-C$_6$-alkyl, or optionally substituted C$_3$-C$_8$-cycloalkyl.

In certain embodiments, the compound of Formula (I) is represented by Formula (II), or a pharmaceutically acceptable salt thereof:

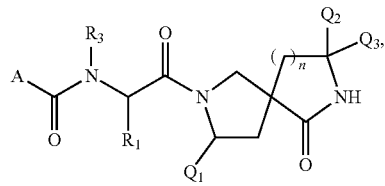

wherein n, A, Q$_1$, Q$_2$, Q$_3$, R$_1$, R$_2$, R$_3$, and n are as previously defined.

In certain embodiments, the compound of Formula (I) is represented by Formula (III), or a pharmaceutically acceptable salt thereof:

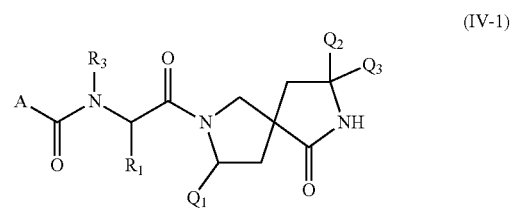

wherein n, A, Q$_1$, Q$_2$, Q$_3$, R$_1$, R$_3$, and n are as previously defined.

In certain embodiments, the compound of Formula (I) is represented by Formula (IV-1), or Formula (IV-2), or a pharmaceutically acceptable salt thereof:

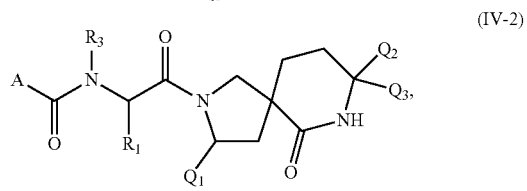

wherein A, Q$_1$, Q$_2$, Q$_3$, R$_1$, and R$_3$ are as previously defined. Preferably, R$_3$ is hydrogen, -Me, -Et, —Pr, -i-Pr, -allyl, —CF$_3$, -CD$_3$, or cyclopropyl; R$_1$ is selected from the following groups:

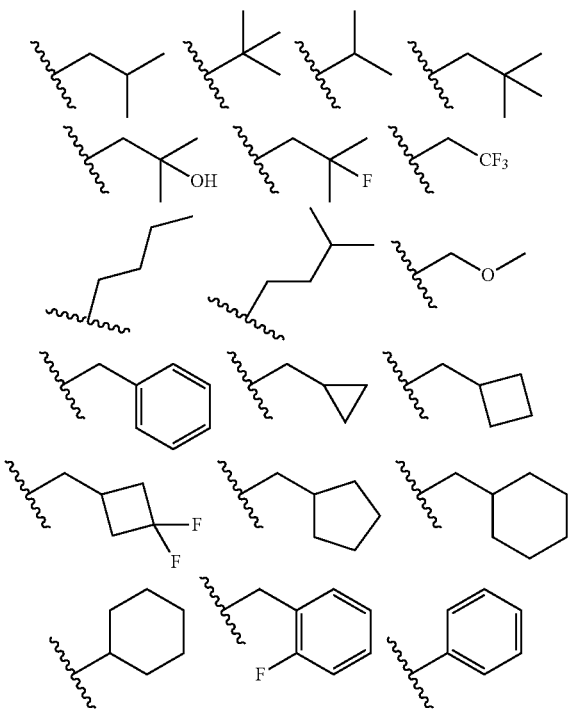

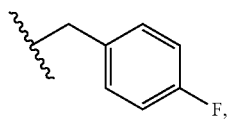

and $Q_1$ is selected from the following groups:

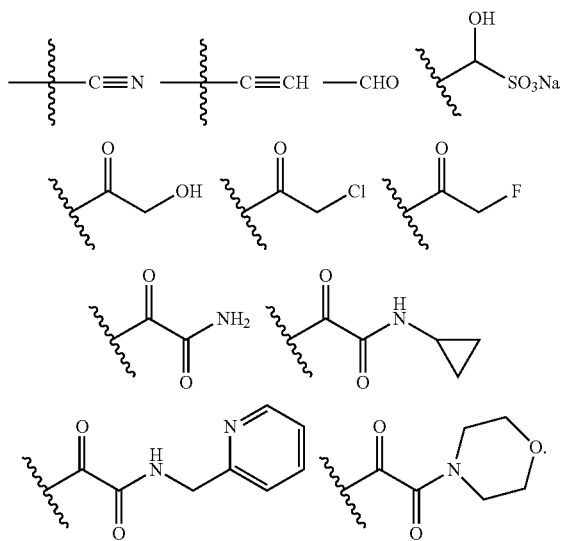

In certain embodiments, the compound of Formula (I) is represented by one of Formulae (V-1)~(V-6), or a pharmaceutically acceptable salt thereof:

(V-1)

(V-2)

(V-3)

(V-4)

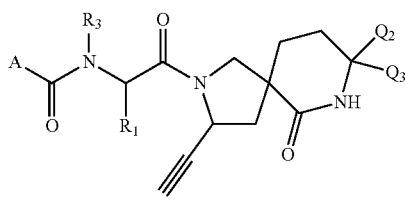

(V-5)

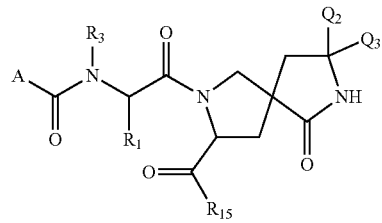

(V-6)

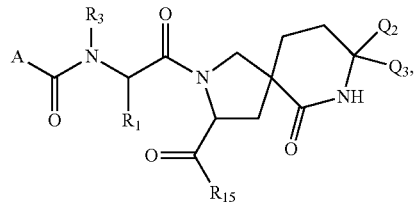

wherein A, $R_{15}$, $Q_2$, $Q_3$, $R_1$, and $R_3$ are as previously defined.

In certain embodiments, the compound of Formula (I) is represented by one of Formulae (VI-1)~(VI-6), or a pharmaceutically acceptable salt thereof:

(VI-1)

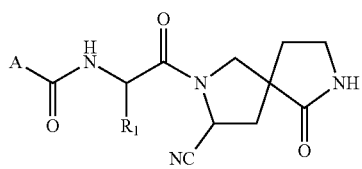

(VI-2)

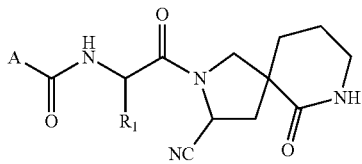

(VI-3)

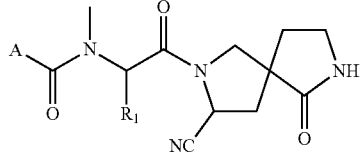

(VI-4)

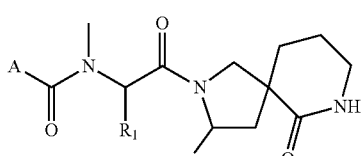

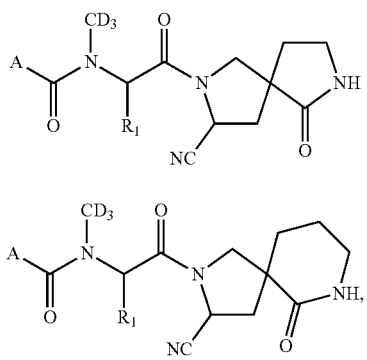
wherein A and R₁ are as previously defined.
In certain embodiments, the compound of Formula (I) is represented by one of Formulae (VI-1)~(VI-6), or a pharmaceutically acceptable salt thereof, wherein, R₁ is selected from:
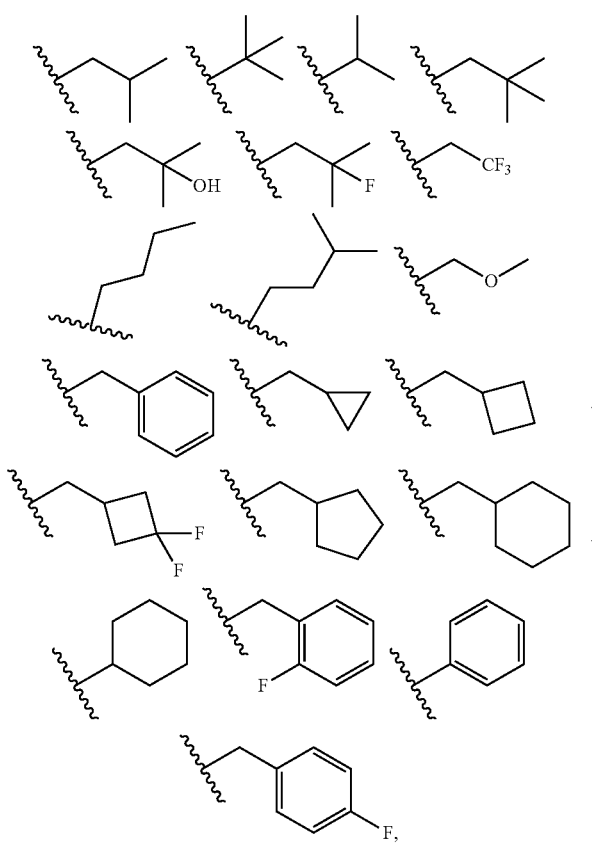
and A is selected from the following groups, and A is optionally substituted:
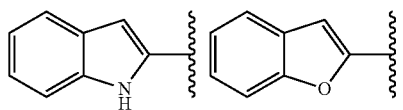
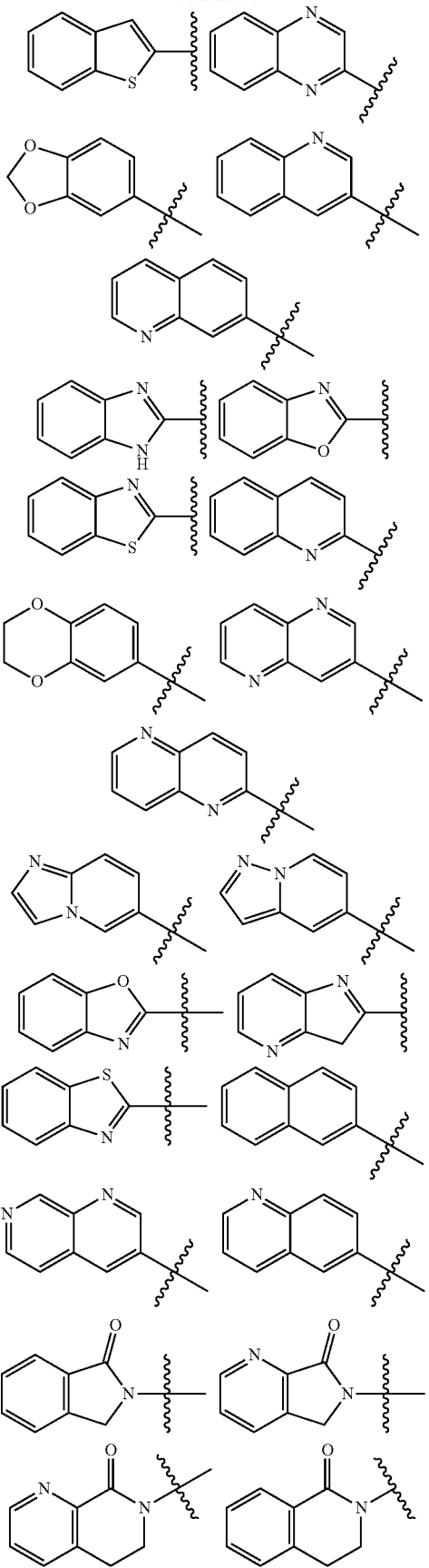

-continued

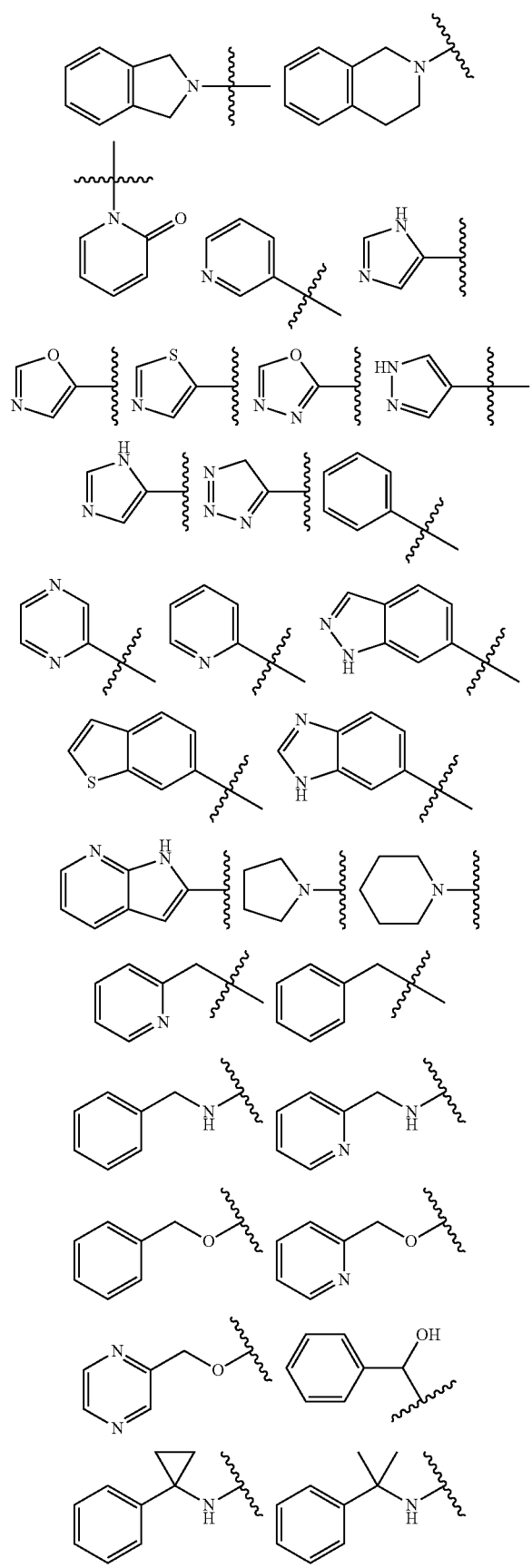

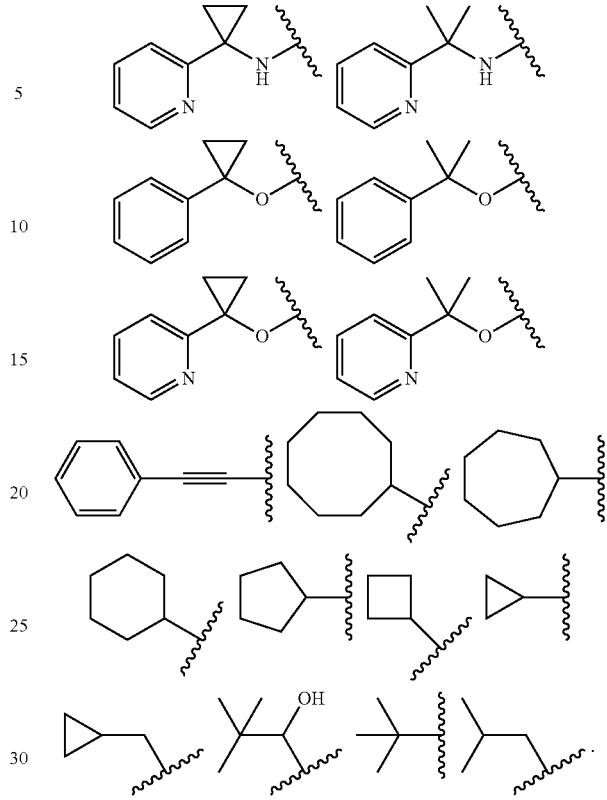

preferably there are 0, 1, 2 or 3 substituents. Preferably the substituent are independently selected from halogen, optionally substituted —$C_1$-$C_3$ alkoxy, optionally substituted —$C_1$-$C_3$ alkyl, optionally substituted —$C_1$-$C_6$ cycloalkyl, optionally substituted aryl, and optionally substituted heteroaryl.

In certain embodiments, the compound of Formula (I) is represented by one of Formulae (VI-1)~(VI-6), or a pharmaceutically acceptable salt, wherein, $R_1$ is selected from:

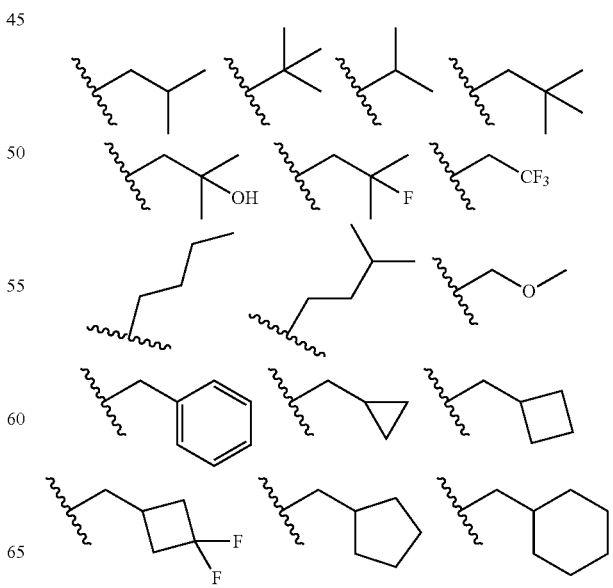

-continued

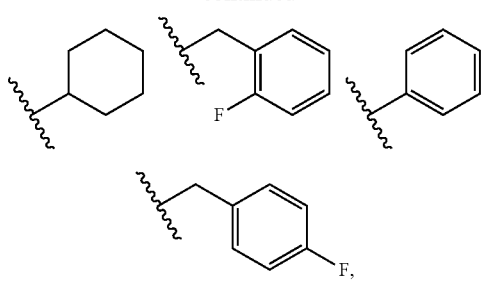

and

A is

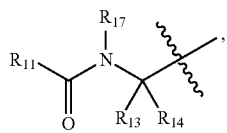

wherein $R_{11}$, $R_{13}$, $R_{14}$, and $R_{17}$ are as previously defined. In certain embodiments, $R_{13}$ and $R_{17}$ are hydrogen, and $R_{14}$ is optionally substituted $C_1$-$C_6$-alkyl, preferably optionally substituted t-butyl, and $R_{11}$ is preferably optionally substituted benzyl, optionally substituted $C_1$-$C_6$-alkyl, or optionally substituted $C_3$-$C_8$-cycloalkyl.

In certain embodiments, the compound of Formula (I) is represented by one of Formulae (VII-1)~(VII-9), or a pharmaceutically acceptable salt thereof:

(VII-1)

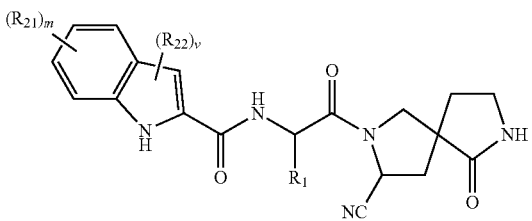

(VII-2)

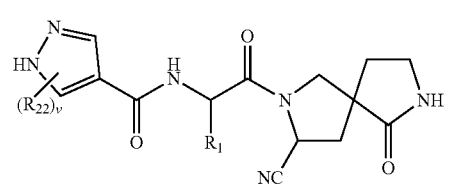

(VII-3)

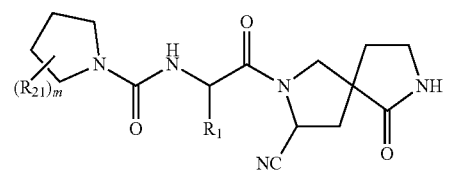

-continued (VII-4)

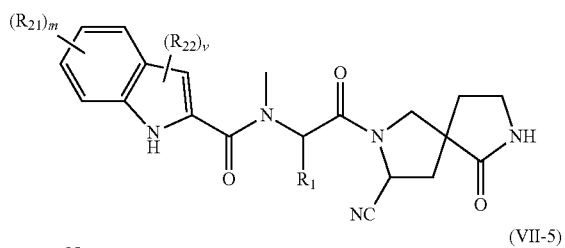

(VII-5)

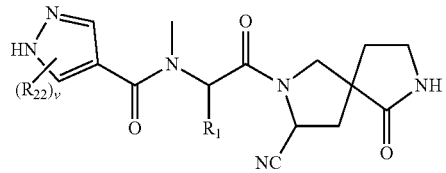

(VII-6)

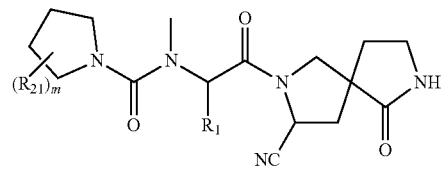

(VII-7)

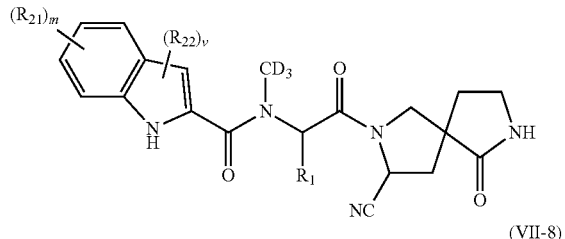

(VII-8)

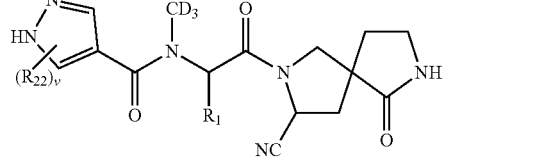

(VII-9)

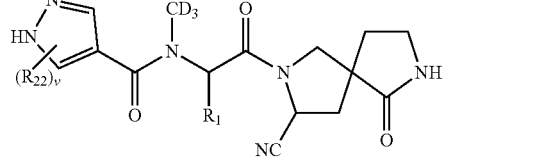

wherein each $R_{21}$ and $R_{22}$ is independently selected from:
1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl; and
11) Optionally substituted heteroaryl;

m is 0, 1, 2, 3, or 4; v is 0, 1, or 2, and $R_1$, $R_{13}$, and $R_{14}$ are as previously defined.

In certain embodiments, the compound of Formula (I) is represented by one of Formulae (VIII-1)~(VIII-9), or a pharmaceutically acceptable salt thereof:

(VIII-1)
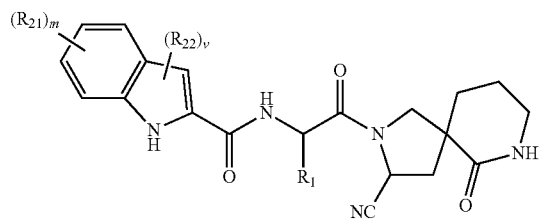

(VIII-2)
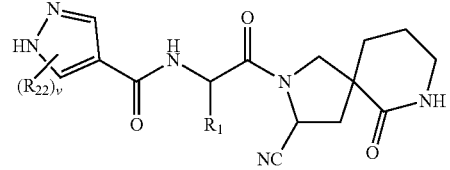

(VIII-3)
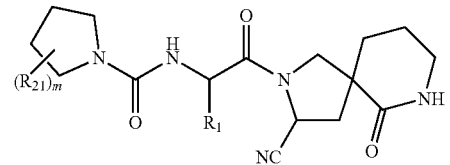

(VIII-4)
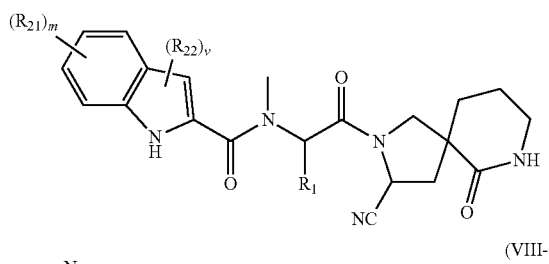

(VIII-5)
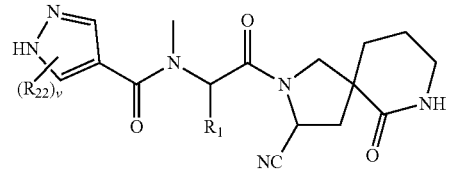

(VIII-6)
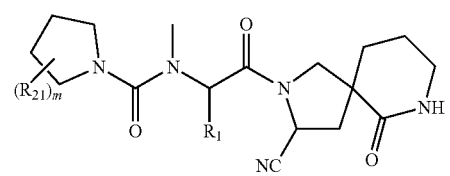

(VIII-7)
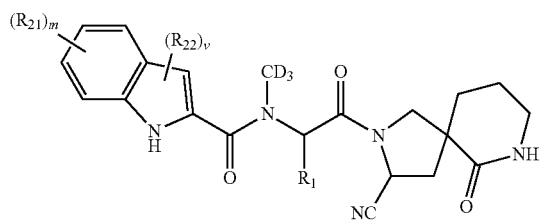

-continued (VIII-8)
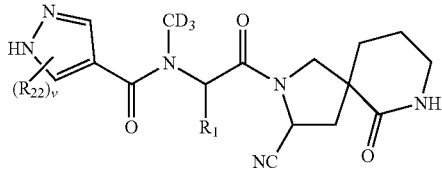

(VIII-9)
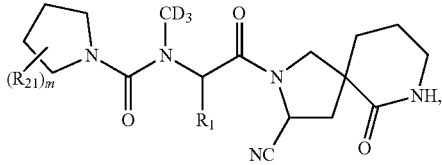

wherein m, v, $R_1$, $R_{21}$ and $R_{22}$ are as previously defined.

In certain embodiments, the compound of Formula (I) is represented by Formula (IX), or a pharmaceutically acceptable salt thereof:

(IX)
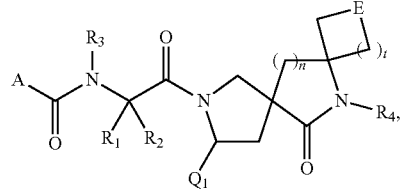

wherein E is —C($R_{13}$)($R_{14}$)—, —N($R_{13}$)—, or —O—; t is 0, 1, 2, 3, or 4, and n, A, $Q_1$, $R_{13}$, $R_{14}$, $R_1$, $R_2$, $R_3$, and $R_4$ are as previously defined.

In certain embodiments, the compound of Formula (I) is represented by Formula (X), or a pharmaceutically acceptable salt thereof:

(X)
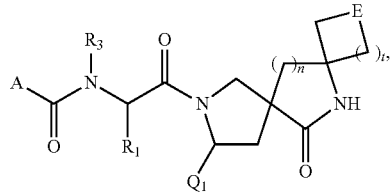

wherein E, t, n, A, $Q_1$, $R_1$, and $R_3$ are as previously defined.

In certain embodiments, the compound of Formula (I) is represented by one of Formulae (XI-1)~(XI-6), or a pharmaceutically acceptable salt thereof:

(XI-1)
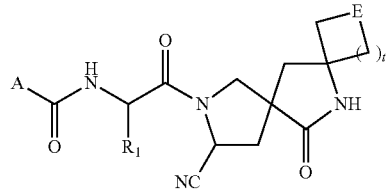

-continued
(XI-2)
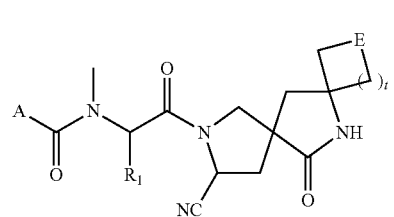
(XI-3)
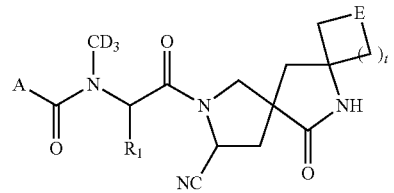
(XI-4)
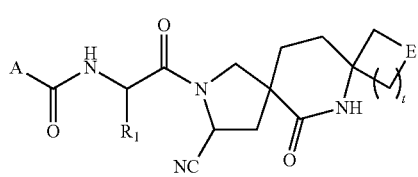
(XI-5)
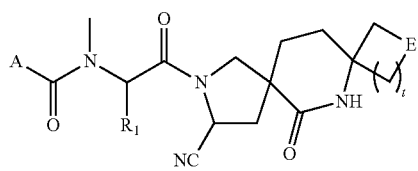
(XI-6)
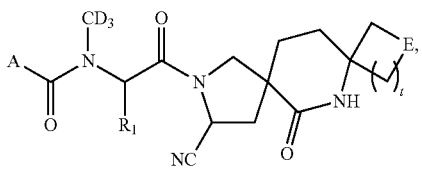
wherein E, t, A, and R₁ are as previously defined.
In certain embodiments, the compound of Formula (I) is represented by one of Formulae (XI-1)~(XI-6), or a pharmaceutically acceptable salt, wherein, R₁ is selected from:
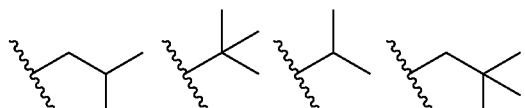
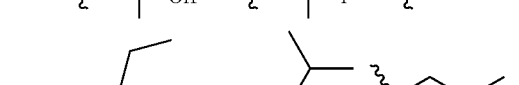
-continued
and A is selected from the following groups, and A is optionally substituted:
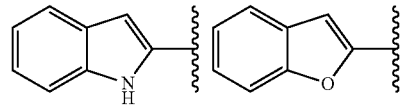
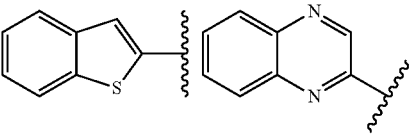
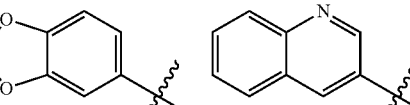
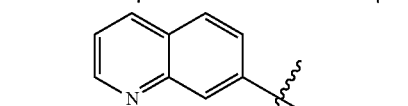
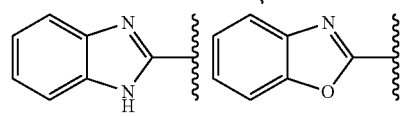
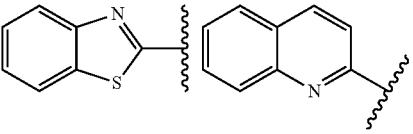
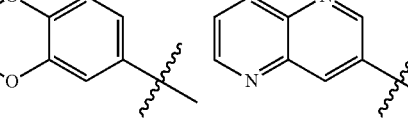
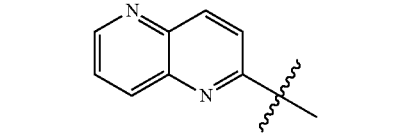
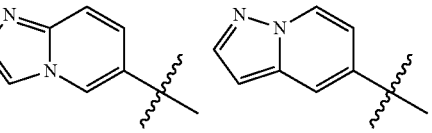

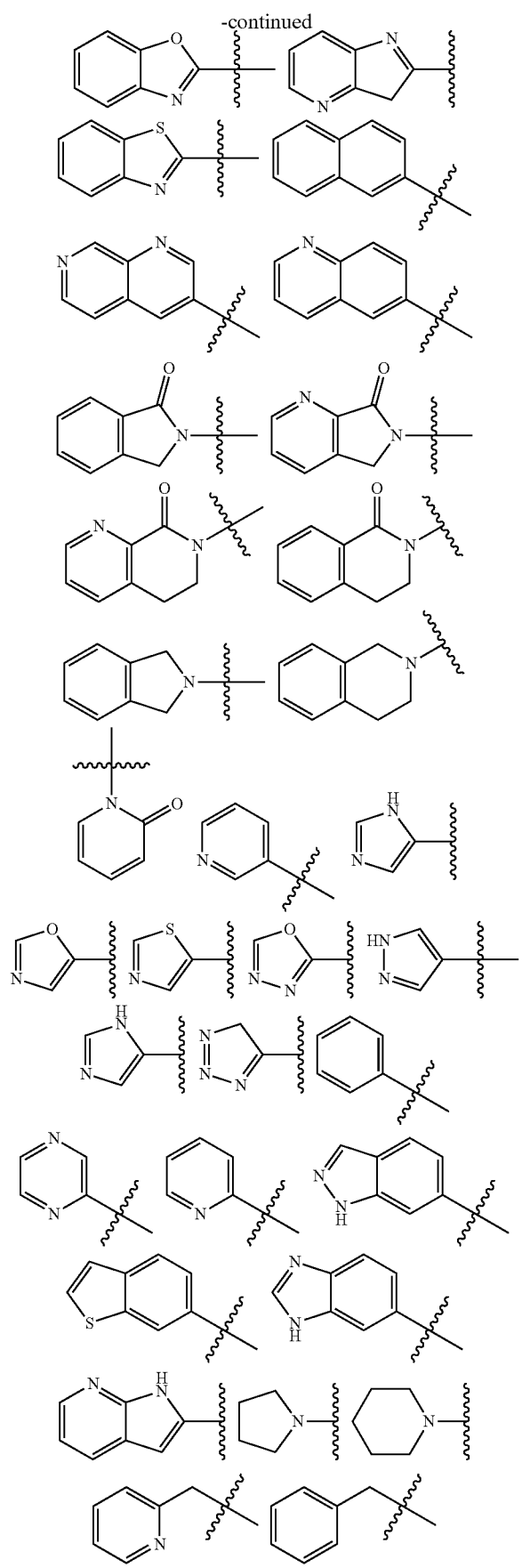
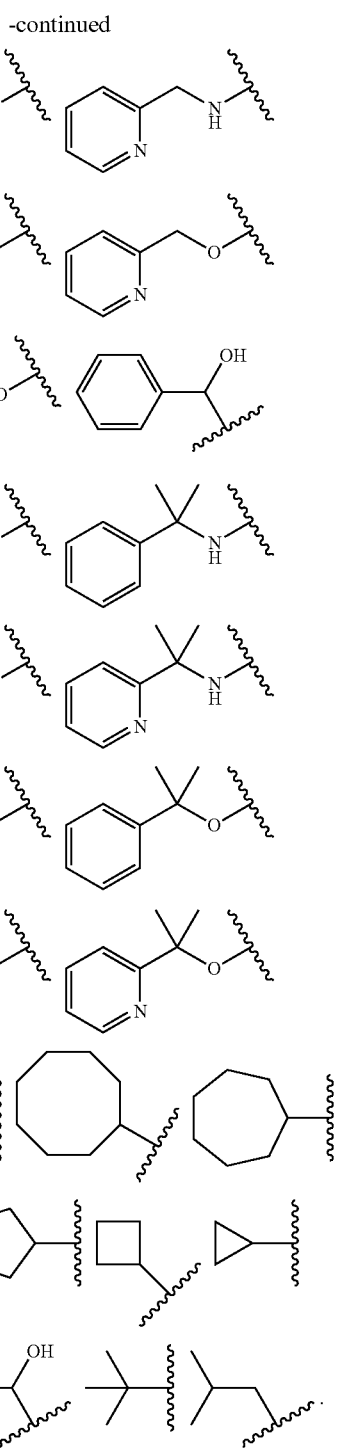

Preferably there are 0, 1, 2 or 3 substituents. Preferably the substituents are independently selected from halogen, optionally substituted —$C_1$-$C_3$ alkoxy, optionally substituted —$C_1$-$C_3$ alkyl, optionally substitiued —$C_1$-$C_3$ cycloalkyl, optionally substituted aryl, optionally substituted heteroaryl.

In certain embodiments, the compound of Formula (I) is represented by one of Formulae (XI-1)~(XI-6), or a pharmaceutically acceptable salt thereof, wherein, $R_1$ is selected from:

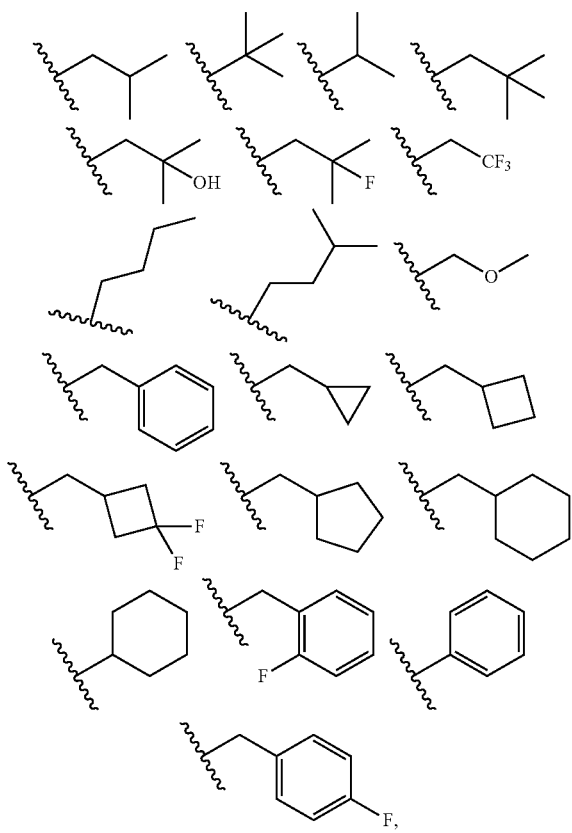

and A is

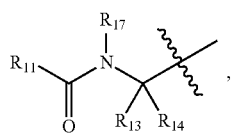

wherein $R_{11}$, $R_{13}$, $R_{14}$, and $R_{17}$ are as previously defined. In certain embodiments, $R_{13}$ and $R_{17}$ are hydrogen, and $R_{14}$ is optionally substituted $C_1$-$C_6$-alkyl, preferably optionally substituted t-butyl, and $R_{11}$ is preferably optionally substituted benzyl, optionally substituted $C_1$-$C_6$-alkyl, or optionally substituted $C_3$-$C_8$-cycloalkyl.

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be achieved by concomitant administration in: (1) a unitary pharmaceutical composition including both compounds; or (2) separate pharmaceutical compositions each including one of the compounds.

In certain embodiments of the combination therapy, the additional therapeutic agent is administered at a lower dose and/or dosing frequency as compared to dose and/or dosing frequency of the additional therapeutic agent required to achieve similar results in treating or preventing coronavirus.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring. Preferred aryl groups are $C_6$-$C_{12}$-aryl groups, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. In certain embodiments, a heteroaryl group is a 5- to 10-membered heteroaryl, such as a 5- or 6-membered monocyclic heteroaryl or an 8- to 10-membered bicyclic heteroaryl. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof. A heteroaryl group can be C-attached or N-attached where possible.

In accordance with the invention, aryl and heteroaryl groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," and "$C_3$-$C_6$ alkyl," refer to alkyl groups containing from 1 to 4, 1 to 6, 1 to 8, 1 to 12, 2 to 4 and 3 to 6 carbon atoms respectively. Examples of alkyl groups include, but are not limited to, methyl, ethyl, propyl, isopropyl, n-butyl, sec-butyl, tert-butyl, n-pentyl, neopentyl, n-hexyl, n-heptyl and n-octyl radicals.

The term "alkenyl" as used herein, refers to straight- or branched-chain hydrocarbon radicals having at least one carbon-carbon double bond. "$C_2$-$C_8$ alkenyl," "$C_2$-$C_{12}$ alkenyl," "$C_2$—$C_4$ alkenyl," "$C_3$-$C_4$ alkenyl," and "$C_3$-$C_6$ alkenyl," refer to alkenyl groups containing from 2 to 8, 2 to 12, 2 to 4, 3 to 4 or 3 to 6 carbon atoms respectively. Alkenyl groups include, but are not limited to, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon triple bond. "$C_2$-$C_8$ alkynyl," "$C_2$-$C_{12}$ alkynyl," "$C_2$-$C_4$ alkynyl," "$C_3$-$C_4$ alkynyl," and "$C_3$-$C_6$ alkynyl," refer to alkynyl groups containing from 2 to 8t, 2 to 12, 2 to 4, 3 to 4 or 3 to 6 carbon atoms respectively. Representative alkynyl groups include, but are not limited to, ethynyl, 2-propynyl, 2-butynyl, heptynyl, octynyl, and the like.

The term "cycloalkyl", as used herein, refers to a monocyclic or polycyclic saturated carbocyclic ring, such as a bi- or tri-cyclic fused, bridged or spiro system. The ring carbon atoms are optionally oxo-substituted or optionally substituted with an exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of cycloalkyl include, but are not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring, such as a bi- or tri-cyclic fused, bridged or spiro system having at least one carbon-carbon double bond. The ring carbon atoms are optionally oxo-substituted or optionally substituted with an exocyclic olefinic double bond. Preferred cycloalkenyl groups include $C_3$-$C_{12}$ cycloalkenyl, $C_4$-$C_{12}$-cycloalkenyl, $C_3$-$C_8$ cycloalkenyl, $C_4$-$C_8$ cycloalkenyl and $C_5$-$C_7$ cycloalkenyl groups. Examples of cycloalkenyl include, but are not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —(CH$_2$)$_n$-phenyl, where n is 1 to 12, preferably 1 to 6 and more preferably 1 or 2. The term "substituted arylalkyl" means an arylalkyl functional group in which the aryl group is substituted. Similarly, the term "heteroarylalkyl" means a functional group wherein an alkylene chain, is attached to a heteroaryl group, e.g., —(CH$_2$)$_n$-heteroaryl, where n is 1 to 12, preferably 1 to 6 and more preferably 1 or 2. The term "substituted heteroarylalkyl" means a heteroarylalkyl functional group in which the heteroaryl group is substituted.

As used herein, the term "alkoxy" is a radical in which an alkyl group having the designated number of carbon atoms is connected to the rest of the molecule via an oxygen atom.

Alkoxy groups include $C_1$-$C_{12}$-alkoxy, $C_1$-$C_8$-alkoxy, $C_1$-$C_6$-alkoxy, $C_1$-$C_4$-alkoxy and $C_1$-$C_3$-alkoxy groups. Examples of alkoxy groups includes, but are not limited to, methoxy, ethoxy, n-propoxy, 2-propoxy (isopropoxy) and the higher homologs and isomers. Preferred alkoxy is $C_1$-$C_3$alkoxy.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" and "heterocycloalkyl" can be used interchangeably and refer to a non-aromatic ring or a polycyclic ring system, such as a bi- or tri-cyclic fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic or heterocycloalkyl groups may be further substituted. A heterocycloalkyl or heterocyclic group can be C-attached or N-attached where possible.

It is understood that any alkyl, alkenyl, alkynyl, alicyclic, cycloalkyl, cycloalkenyl, aryl, heteroaryl, heterocyclic, aliphatic moiety or the like described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —$C_1$, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —NO$_2$, —N$_3$, —CN, —NH$_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$- alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_8$ alkenyl, —CO$_2$—C$_2$-C$_8$ alkynyl, —CO$_2$—C$_3$-C$_{12}$-cycloalkyl, —CO$_2$-aryl, —CO$_2$-heteroaryl, —CO$_2$-heterocyloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH— heterocycloalkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)— heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, —NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH$_2$, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH— heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$—C$_1$-C$_{12}$-alkyl, —SO$_2$—C$_2$-C$_8$-alkenyl, —SO$_2$—C$_2$-C$_8$-alkynyl, —SO$_2$—C$_3$-C$_{12}$-cycloalkyl, —SO$_2$-aryl, —SO$_2$-heteroaryl, —SO$_2$-heterocycloalkyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S-heteroaryl, —S— heterocycloalkyl, or methylthiomethyl. In certain embodiments, the substituents are independently selected from halo, preferably C$_1$ and F; C$_1$-C$_4$-alkyl, preferably methyl and ethyl; halo-C$_1$-C$_4$-alkyl, such as fluoromethyl, difluoromethyl, and trifluoromethyl; C$_2$-C$_4$-alkenyl; halo-C$_2$-C$_4$-alkenyl; C$_3$-C$_6$-cycloalkyl, such as cyclopropyl; C$_1$-C$_4$-alkoxy, such as methoxy and ethoxy; halo-C$_1$-C$_4$-alkoxy, such as fluoromethoxy, difluoromethoxy, and trifluoromethoxy; —CN; —OH; NH$_2$; C$_1$-C$_4$-alkylamino; di(C$_1$-C$_4$-alkyl)amino; and NO$_2$. It is understood that an aryl, heteroaryl, alkyl, alkenyl, alkynyl, cycloalkyl, or heterocycloalkyl in a substituent can be further substituted. In certain embodiments, a substituent in a substituted moiety is additionally optionally substituted with one or more groups, each group being independently selected from C$_1$-C$_4$-alkyl; —CF$_3$, —OCH$_3$, —OCF$_3$, —F, —C$_1$, —Br, —I, —OH, —NO$_2$, —CN, and —NH$_2$. Preferably, a substituted alkyl group is substituted with one or more halogen atoms, more preferably one or more fluorine or chlorine atoms. The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an element includes all isotopes of that element so long as the resulting compound is pharmaceutically acceptable. In certain embodiments, the isotopes of an element are present at a particular position according to their natural abundance. In other embodiments, one or more isotopes of an element at a particular position are enriched beyond their natural abundance.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including, but not limited to mesylate, tosylate, triflate, p-nitrobenzoate, phosphonate groups.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in P. G. M. Wuts, Greene+s *Protective Groups in Organic Synthesis,* 5th edition, John Wiley & Sons, Hoboken, NJ (2014). Examples of hydroxyl protecting groups include, but not limited to, benzyloxycarbonyl, 4-methoxybenzyloxycarbonyl, tert-butoxy-carbonyl, isopropoxycarbonyl, diphenyl-methoxycarbonyl, 2,2,2-trichloroethoxycarbonyl, allyloxy-carbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including but not limited to, benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs. Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in P. G. M. Wuts, Greene's *Protective Groups in Organic Synthesis,* 5th edition, John Wiley & Sons, Hoboken, NJ (2014). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject," as used herein, refers to an animal. Preferably, the animal is a mammal. More preferably, the mammal is a human. A subject also refers to, for example, a dog, cat, horse, cow, pig, guinea pig, fish, bird and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

In certain embodiments, the present invention provides a method of treating or preventing a viral infection in a subject in need thereof, comprising administering to the subject a therapeutically effective amount of a compound of Formula (I) or a pharmaceutically acceptable salt thereof. The viral infection is preferably a coronavirus infection. In certain embodiments, the coronavirus is SARS-CoV-1, SARS-CoV-2, or MERS-CoV. Preferably the coronavirus is SARS-CoV-2.

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (Iysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-1gE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, antheimintic agents, antimalarial agents, antiprotozoal agents, antitubercuiosis agents, and antiviral agents, including those listed at https://www.drugs.com/drug-class/anti-infectives.html. In general, combination therapy is typically preferred over alternation therapy because it induces multiple simultaneous stresses on the virus.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Although the invention has been described with respect to various preferred embodiments, it is not intended to be limited thereto, but rather those skilled in the art will recognize that variations and modifications may be made therein which are within the spirit of the invention and the scope of the appended claims.

Abbreviations

Abbreviations which may be used in the descriptions of the scheme and the examples that follow are: Ac for acetyl; AcOH for acetic acid; $Boc_2O$ for di-tert-butyl-dicarbonate; Boc for t-butoxycarbonyl; Bz for benzoyl; Bn for benzyl; t-BuOK for potassium tert-butoxide; Brine for sodium chloride solution in water; CDI for carbonyldiimidazole; DCM or $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; DBU for 1,8-diazabicyclo[5.4.0]-undec-7-ene; DEAD for diethylazodicarboxylate; DIAD for diisopropyl azodicarboxylate; DIPEA or $(i-Pr)_2EtN$ for N,N,-diisopropylethyl amine; DMP or Dess-Martin periodinane for 1,1,2-tris(acetyloxy)-1,2-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EtOAc for ethyl acetate; EtOH for ethanol; $Et_2O$ for diethyl ether; HATU for O-(7-azabenzotriazol-2-yl)-N,N,N',N',-tetramethyluronium Hexafluorophosphate; HCl for hydrogen chloride; $K_2CO_3$ for potassium carbonate; n-BuLi for n-butyl lithium; DDQ for 2,3-dichloro-5,6-dicyano-1,4-benzoquinone; LDA for lithium diisopropylamide; LiTMP for lithium 2,2,6,6-tetramethyl-piperidinate; MeOH for methanol; Mg for magnesium; MOM for methoxymethyl; Ms for mesyl or $—SO_2—CH_3$; NaHMDS for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4Cl$ for ammonium chloride; Ni for nickel; OH for hydroxyl; $OsO_4$ for osmium tetroxide; OTf for triflate; PPA for polyphosphoric acid; PTSA for p-toluenesulfonic acid; PPTS for pyridinium p-toluenesulfonate; TBAF for tetrabutylammonium fluoride; TEA or $Et_3N$ for triethylamine; TES for triethylsilyl; TESCl for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or $PPh_3$ for triphenyl-phosphine; Tos or Ts for tosyl or $—SO_2—C_6H_4CH_3$; $Ts_2O$ for tolylsulfonic anhydride or tosyl-anhydride; TsOH for p-tolylsulfonic acid; Pd for palladium; Ph for phenyl; $Pd_2(dba)_3$ for tris(diben-zylideneacetone) dipalladium (0); $Pd(PPh_3)_4$ for tetrakis(triphenylphosphine)-palladium (0); $PdCl_2(PPh_3)_2$ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; and TMSCl for trimethylsilyl chloride.

Synthetic Methods

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

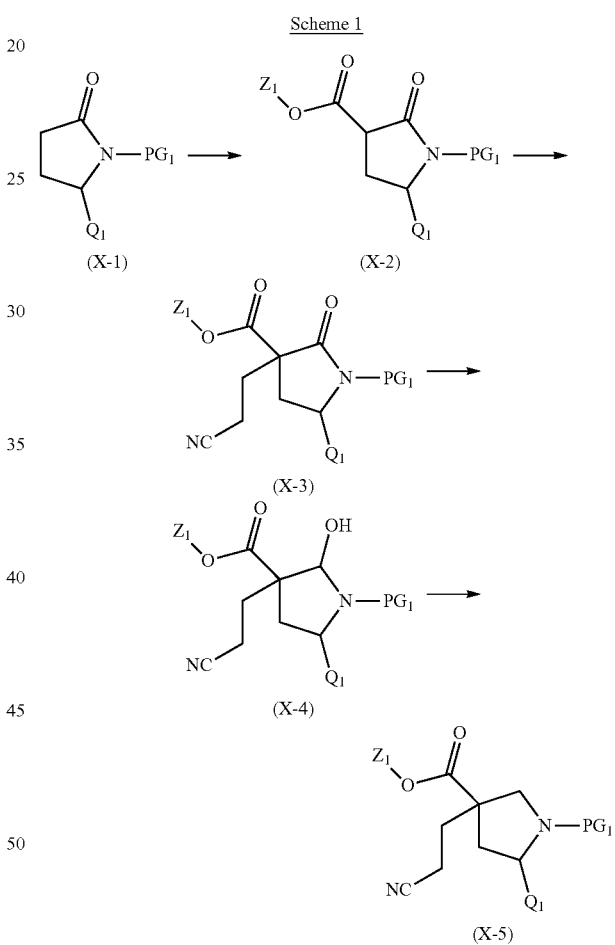

Scheme 1

Scheme 1 illustrates a general method to prepare the compound of formula (X-5) from lactam (X-1), wherein $Q_1$ is as previously defined and $PG_1$ is a carbonyl-containing protecting group. Compound (X-1) can be reacted with an electrophilic reagent including, but not limited to ethyl chloroformate or benzyl chloroformate in the presence of a basic compound including, but not limited to LHMDS, KHMDS, or NaH, to produce compound (X-2), whereby $Z_1$ is defined as optionally substituted alkyl or optionally substituted aryl. Compound (X-2) is reacted with a nitrile reagent including, but not limited to acrylonitrile in the presence of a basic compound including, but not limited to DBU or triethylamine, to produce compound (X-3). Compound (X-3) is reacted in a reduction reaction with reducing agents including, but not limited to lithium triethylborohydride or lithium aluminium hydride, to produce compound (X-4). Compound (X-4) can be further reduced using reagents including, but not limited to triethylsilane, sodium borohydride, or TFA to produce compound (X-5).

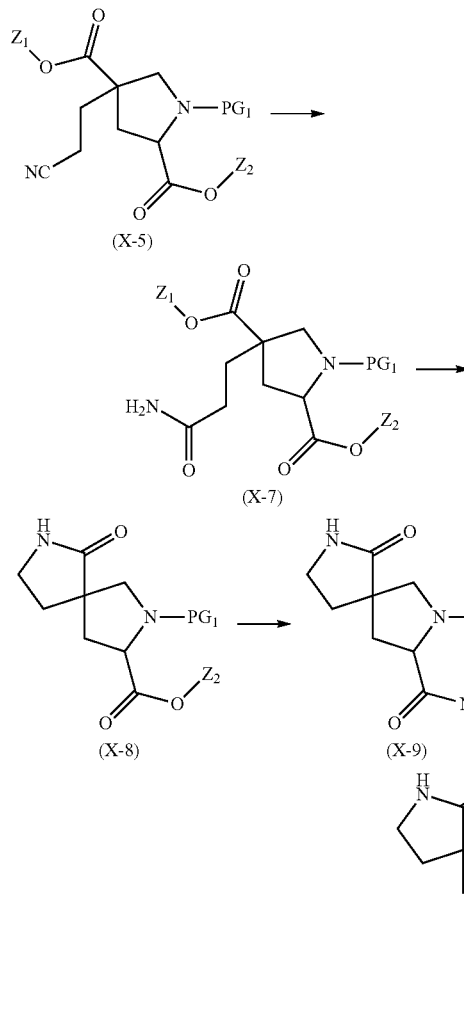

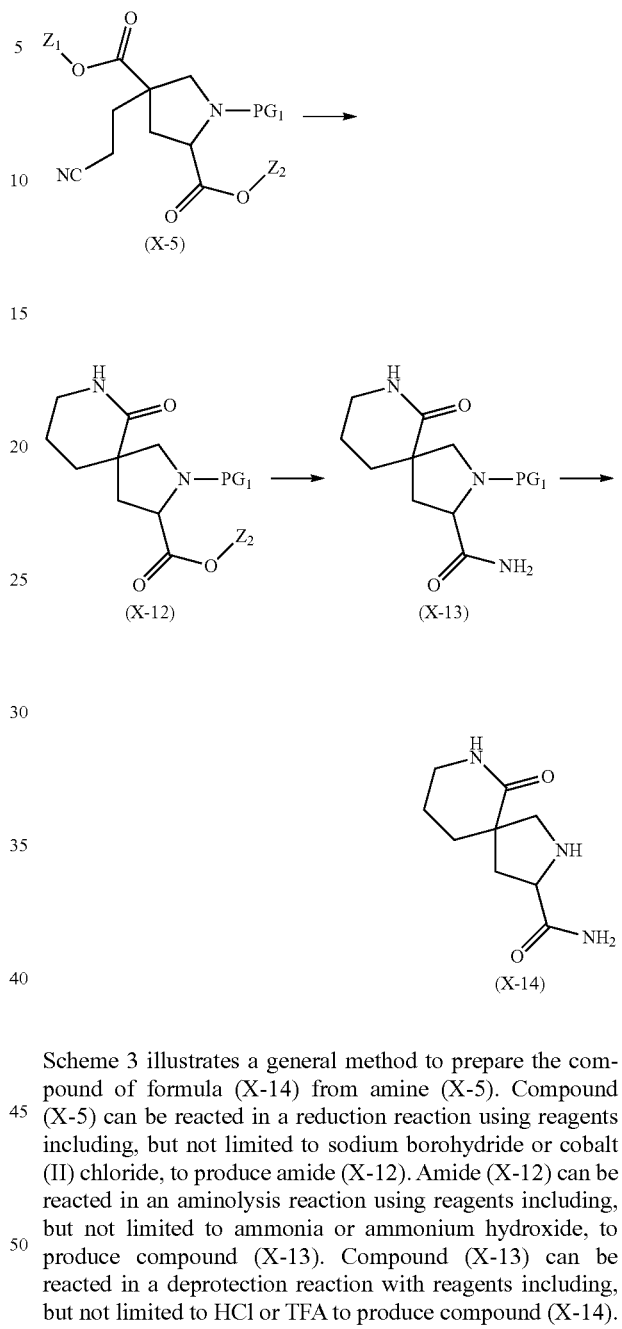

Scheme 2 illustrates a general method to prepare the compound of formula (X-10) from amine (X-5). Compound (X-5) can be reacted in a hydration reaction using reagents including, but not limited to Parkins catalyst or water, to produce amide (X-7). Amide (X-7) can be reacted in a rearrangement reaction using reagents including, but not limited to [bis(trifluoroacetoxy)iodo]benzene to produce lactam (X-8). Lactam (X-8) can be reacted in an aminolysis reaction using reagents including, but not limited to ammonia or ammonium hydroxide, to produce compound (X-9). Compound (X-9) can be reacted in a deprotection reaction with reagents including, but not limited to HCl or TFA to produce compound (X-10).

Scheme 3 illustrates a general method to prepare the compound of formula (X-14) from amine (X-5). Compound (X-5) can be reacted in a reduction reaction using reagents including, but not limited to sodium borohydride or cobalt (II) chloride, to produce amide (X-12). Amide (X-12) can be reacted in an aminolysis reaction using reagents including, but not limited to ammonia or ammonium hydroxide, to produce compound (X-13). Compound (X-13) can be reacted in a deprotection reaction with reagents including, but not limited to HCl or TFA to produce compound (X-14).

Scheme 4

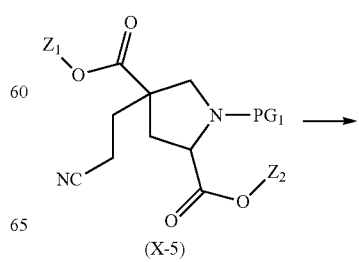

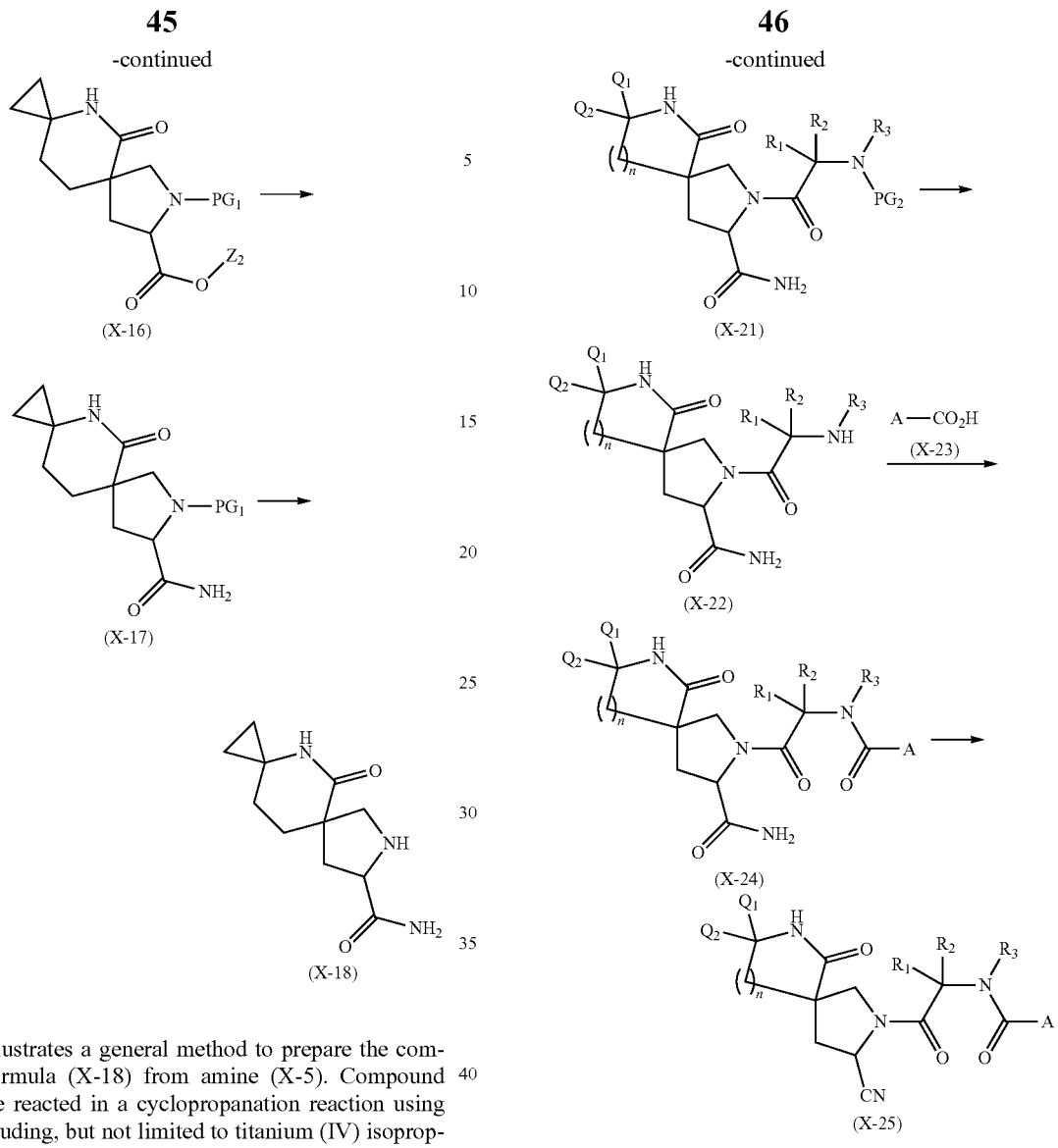

Scheme 4 illustrates a general method to prepare the compound of formula (X-18) from amine (X-5). Compound (X-5) can be reacted in a cyclopropanation reaction using reagents including, but not limited to titanium (IV) isopropoxide or ethyl magnesium bromide, to produce amide (X-16). Amide (X-12) can be reacted in an aminolysis reaction using reagents including, but not limited to ammonia or ammonium hydroxide, to produce compound (X-17). Compound (X-17) can be reacted in a deprotection reaction with reagents including, but not limited to HCl or TFA to produce compound (X-18).

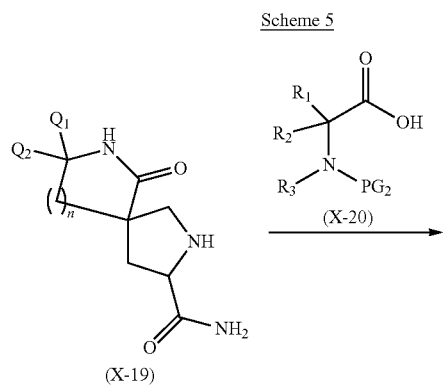

Scheme 5 illustrates a general method to prepare the compound of formula (X-25) from amine (X-19), whereby $Q_1$, $Q_2$, and n are previously defined. Compound (X-19) can be reacted in an amidation reaction with compound (X-20), whereby $R_1$, $R_2$, and $R_3$ are previously defined and $PG_2$ is defined as a carbonyl containing protecting group, that is mediated by a coupling reagent including, but not limited to HATU, HOBT, or DCC, to produce amide (X-21). Amide (X-21) can be reacted in a deprotection reaction with reagents including, but not limited to HCl or TFA to produce compound (X-22). Compound (X-22) can be reacted in an amidation reaction with compound (X-23), whereby A is previously defined, that is mediated by a coupling reagent including, but not limited to HATU, HOBT, or DCC, to produce amide (X-24). Amide (X-24) is converted to compound (X-25) under dehydration conditions using reagents including, but not limited to: TFAA/Et$_3$N, or Pd(OCOCF$_3$)$_2$/Cl$_2$CHCN.

EXAMPLES

The compounds and processes of the present invention will be better understood in connection with the following examples, which are intended as an illustration only and not limiting of the scope of the invention. Starting materials were either available from a commercial vendor or produced by methods well known to those skilled in the art.

While this invention has been particularly shown and described with references to preferred embodiments thereof, it will be understood by those skilled in the art that various changes in form and details may be made therein without departing from the scope of the invention encompassed by the appended claims.

General Conditions:

Mass spectra were run on LC-MS systems using electrospray ionization. These were Agilent 1290 Infinity II systems with an Agilent 6120 Quadrupole detector. Spectra were obtained using a ZORBAX Eclipse XDB-$C_{18}$ column (4.6×30 mm, 1.8 micron). Spectra were obtained at 298K using a mobile phase of 0.1% formic acid in water (A) and 0.1% formic acid in acetonitrile (B). Spectra were obtained with the following solvent gradient: 5% (B) from 0-1.5 min, 5-95% (B) from 1.5-4.5 min, and 95% (B) from 4.5-6 min. The solvent flowrate was 1.2 mL/min. Compounds were detected at 210 nm and 254 nm wavelengths. [M+H]$^+$ refers to mono-isotopic molecular weights.

NMR spectra were run on a Bruker 400 MHz spectrometer. Spectra were measured at 298K and referenced using the solvent peak. Chemical shifts for $^1$H NMR are reported in parts per million (ppm).

Compounds were purified via reverse-phase high-performance liquid chromatography (RPHPLC) using a Gilson GX-281 automated liquid handling system. Compounds were purified on a Phenomenex Kinetex EVO $C_{18}$ column (250×21.2 mm, 5 micron), unless otherwise specified. Compounds were purified at 298K using a mobile phase of water (A) and acetonitrile (B) using gradient elution between 0% and 100% (B), unless otherwise specified. The solvent flowrate was 20 mL/min and compounds were detected at 254 nm wavelength.

Alternatively, compounds were purified via normal-phase liquid chromatography (NPLC) using a Teledyne ISCO Combiflash purification system. Compounds were purified on a REDISEP silica gel cartridge. Compounds were purified at 298K and detected at 254 nm wavelength.

Ex. 1: Synthesis of N—((S)-1-((3S,5S)-3-cyano-6-oxo-2,7-diazaspiro[4.4]nonan-2-yl)-4-fluoro-4-methyl-1-oxopentan-2-yl)-4,6-difluoro-N-methyl-1H-indole-2-carboxamide

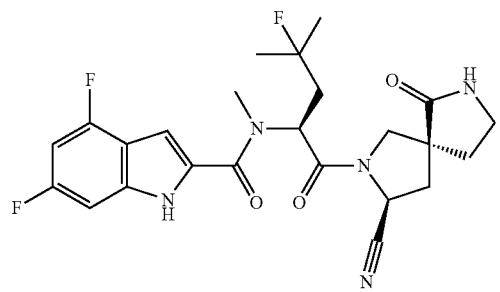 [SMILES: CN(C(=O)c1cc2c(F)cc(F)cc2[nH]1)[C@@H](CC(C)(C)F)C(=O)N1C[C@]2(CCNC2=O)C[C@H]1C#N]

Step 1

In a 500 mL flame dried round bottom flask equipped with a stir bar, 1-(tert-butyl) 2-methyl (S)-5-oxopyrrolidine-1,2-dicarboxylate (CAS: 108963-96-8, 6.00 g, 1.0 equiv) was dissolved in anhydrous tetrahydrofuran (99.0 mL, 0.25M) under a nitrogen atmosphere. The solution was cooled to –78° C. using a dry ice and acetone bath. Lithium bis(trimethylsilyl)amide (49.3 mL, 1M THF, 2.0 equiv) was then added slowly in small portions. The resulting mixture was stirred for 1 h at –78° C. Ethyl chloroformate (2.84 mL, 1.2 equiv) was subsequently added, and the reaction was allowed to reach room temperature. After 17.5 h, saturated aqueous ammonium chloride (100 mL) was added to quench the reaction. The aqueous phase was extracted with ethyl acetate and the combined organic layers were dried over magnesium sulfate. Upon concentration, the crude residue was purified by silica gel column chromatography (gradient elution, 0 to 45% ethyl acetate/cyclohexane to afford 1-(tert-butyl) 4-ethyl 2-methyl (2S)-5-oxopyrrolidine-1,2,4-tricarboxylate (6.52 g, 84% yield) as an uncharacterized mixture of cis- and trans-diastereomers (2:1 dr). ESI MS m/z=338.0 [M+Na]$^+$.

Step 2

In a 250 mL round bottom flask equipped with a stir bar, (2S)-5-oxopyrrolidine-1,2,4-tricarboxylate (7.64 g, 1.0 equiv) was dissolved in methyl tert-butyl ether (97.0 mL, 0.25M). Next, 1-(3,5-bis(trifluoromethyl)phenyl)-3-((1R,2R)-2-(dimethylamino)cyclohexyl)thiourea (CAS: 620960-26-1, 4.01 g, 40 mol %) was added, followed by acrylonitrile (6.38 mL, 4.0 equiv). The resulting mixture was stirred at room temperature for 65 h. At this time a white solid had precipitated from the reaction mixture and it was collected via filtration. The solid was slurried with 200 mL of a 3:1 mixture of cyclohexane/MTBE and then re-collected via filtration to provide 1-(tert-butyl) 4-ethyl 2-methyl (2S,4S)-4-(2-cyanoethyl)-5-oxopyrrolidine-1,2,4-tricarboxylate (5.39 g, >20:1 dr, 60% yield).

Step 3

In a flame dried 250 mL round bottom flask equipped with a stir bar, 1-(tert-butyl) 4-ethyl 2-methyl (2S,4S)-4-(2-cyanoethyl)-5-oxopyrrolidine-1,2,4-tricarboxylate (2.66 g, 1.0 equiv) was dissolved in a mixture of THF and DCM [THF (28.6 mL), DCM (7.5 mL), 3.8:1 THF/DCM, 0.2M] at –78° C. under a nitrogen atmosphere. Next, lithium triethylborohydride (7.2 mL, 1M THF, 1.15 equiv) was added. After stirring for 1 h and 15 min at –78° C., LCMS analysis of an aliquot of the reaction mixture indicated incomplete consumption of the starting material, and additional lithium triethylborohydride (7.22 mL, 1M THF, 1.15 equiv) was added. After stirring for an additional 30 min at –78° C., the reaction mixture was quenched with hydrogen peroxide (6.0 mL, 30 wt %, 7.9 equiv) and further diluted with saturated aqueous sodium bicarbonate (100 mL). The aqueous phase was extracted with ethyl acetate (3×80 mL) and the combined organic layers were dried over magnesium sulfate. Concentration afforded crude 1-(tert-butyl) 4-ethyl 2-methyl (2S,4S)-4-(2-cyanoethyl)-5-hydroxypyrrolidine-1,2,4-tricarboxylate that was used in the subsequent step without purification. ESI MS m/z=393.2 [M+Na]$^+$.

Step 4

The crude 1-(tert-butyl) 4-ethyl 2-methyl (2S,4S)-4-(2-cyanoethyl)-5-hydroxypyrrolidine-1,2,4-tricarboxylate (1.0 equiv) produced in Step 3 was dissolved in DCM (28.8 mL, 0.25M) in a 100 mL round bottom flask equipped with a stir bar under a nitrogen atmosphere. The resulting solution was cooled in an ice water bath, and triethylsilane (4.61 mL, 4.0 equiv) was added, followed by trifluoroacetic acid (2.22 mL, 4.0 equiv). After 3.5 h, LCMS analysis of an aliquot of the reaction mixture indicated incomplete consumption of starting material and additional triethylsilane (2.3 mL, 2.0 equiv) and trifluoroacetic anhydride (1.11 mL, 2.0 equiv) were added. After 1 h, the reaction mixture was transferred portionwise to 200 mL of ice-cold saturated aqueous sodium bicarbonate. The aqueous phase was extracted with DCM and the combined organic layers were dried over magnesium sulfate. Upon concentration, the crude residue was purified by silica gel column chromatography (gradient elution, 0 to 50% ethyl acetate/cyclohexane) to afford 1-(tert-butyl) 4-ethyl 2-methyl (2S,4S)-4-(2-cyanoethyl)pyrrolidine-1,2,4-tricarboxylate (1.18 g, 46% yield over two steps). ESI MS m/z=377.2 [M+Na]$^+$.

Step 5

In a 40 mL vial equipped with a stir bar and pressure release septum, 1-(tert-butyl) 4-ethyl 2-methyl (2S,4S)-4-(2-cyanoethyl)pyrrolidine-1,2,4-tricarboxylate (250.0 mg, 1.0 equiv) was dissolved in a mixture of 1,4-dioxane (2.65 mL) and water (0.88 mL). Parkins catalyst (CAS: 173416-05-2, 10.6 mg, 3.5 mol %) was then added, and the mixture was heated at 75° C. in the sealed vial for 2 h and 45 min. The mixture was then cooled to room temperature, concentrated, re-dissolved in DCM, and passed through celite using DCM to rinse. Concentration afforded 1-(tert-butyl) 4-ethyl 2-methyl (2S,4S)-4-(3-amino-3-oxopropyl)pyrrolidine-1,2,4-tricarboxylate as a white solid that was used in the subsequent step without further purification.

Step 6

In a 40 mL vial equipped with a stir bar, 1-(tert-butyl) 4-ethyl 2-methyl (2S,4S)-4-(3-amino-3-oxopropyl)pyrrolidine-1,2,4-tricarboxylate (1.0 equiv) prepared in Step 5 was dissolved in a mixture of MeCN and water [MeCN (2.12 mL), water (0.71 mL), 3:1 MeCN/water, 0.25M]. The solution was cooled to 10° C., and [bis(trifluoroacetoxy)iodo] benzene (334.0 mg, 1.1 equiv) was added in a single portion. The resulting mixture was allowed to reach room temperature. After 18 h, high conversion to the intermediate primary amine was observed by LCMS. The reaction mixture was cooled in an ice water bath and MeOH (1.0 mL) was added followed by ammonium hydroxide (1.28 mL, 30 wt %). The ice water bath was maintained and the mixture was allowed to stir for 4 h. The reaction was diluted with ethyl acetate (30 mL) and water (5 mL) and the aqueous phase was extracted with ethyl acetate. The combined organic layers were dried over magnesium sulfate. Upon concentration, the crude residue was purified by silica gel column chromatography (gradient elution, 0 to 15% MeOH/DCM) to afford 2-(tert-butyl) 3-methyl (3S,5S)-6-oxo-2,7-diazaspiro[4.4]nonane-2,3-dicarboxylate (151.0 mg, 71% over two steps). ESI MS m/z=299.1 [M+H]$^+$.

Step 7

In a 35 mL high pressure reaction tube equipped with a stir bar, 2-(tert-butyl) 3-methyl (3S,5S)-6-oxo-2,7-diazaspiro[4.4]nonane-2,3-dicarboxylate (151.0 mg, 1.0 equiv) was dissolved in methanolic ammonia (3.62 mL, 7M NH$_3$, 50 equiv). The resulting mixture was heated at 60° C. for 88 h. The mixture was cooled to room temperature, concentrated, and the crude residue was purified by silica gel column chromatography (gradient elution, 0 to 20% MeOH/DCM) to afford tert-butyl (3S,5S)-3-carbamoyl-6-oxo-2,7-diazaspiro[4.4]nonane-2-carboxylate as a white solid (44.3 mg). ESI MS m/z=284.2 [M+H]$^+$.

Step 8

In a 40 mL vial equipped with a stir bar, tert-butyl (3S,5S)-3-carbamoyl-6-oxo-2,7-diazaspiro[4.4]nonane-2-carboxylate (44.3 mg, 1.0 equiv) was treated with HCl (4M/dioxane, 0.78 mL, 20 equiv). The resulting mixture was stirred for 1.5 h and then concentrated to afford (3S,5S)-6-oxo-2,7-diazaspiro[4.4]nonane-3-carboxamide hydrochloride as a white solid that was used without purification. ESI MS m/z=184.1 [M+H]$^+$. $^1$H NMR (400 MHz, DMSO-d$_6$, δ ppm): δ 4.29-4.21 (m, 1H), 3.29-3.17 (m, 4H), 2.36 (dd, J=12.8, 7.2 Hz, 1H), 2.19-2.02 (m, 2H), 1.90 (dd, J=12.8, 11.0 Hz, 1H).

Step 9

In a 40 mL vial equipped with a stir bar, (3S,5S)-6-oxo-2,7-diazaspiro[4.4]nonane-3-carboxamide hydrochloride (1.0 equiv) was combined with (S)-2-((tert-butoxycarbonylmethyl)amino)-4-fluoro-4-methylpentanoic acid (CAS: 156047-44-8, 40.9 mg, 1.0 equiv) in a mixture of DCM and DMF [DCM (1.3 mL), DMF (0.50 mL), 4:1.5 DCM/DMF, 0.086M]. The mixture was cooled in an ice water bath, and N-methylmorpholine (55 μL, 3.2 equiv) was added. The mixture was stirred until homogenous, and HATU (59.0 mg, 1.0 equiv) was added. The reaction mixture was allowed to warm to room temperature and was stirred for an additional 14 h before being diluted with DCM (20 mL). The organic layer was washed twice with 1.2M HCl (4 mL) and once with brine (4 mL) and was then passed through a phase separator and concentrated. The crude residue was purified by RPHPLC to afford tert-butyl ((S)-1-((3S,5S)-3-carbamoyl-6-oxo-2,7-diazaspiro[4.4]nonan-2-yl)-4-fluoro-4-methyl-1-oxopentan-2-yl)(methyl)carbamate as a white solid (57.1 mg, 86% yield). ESI MS m/z=429.3 [M+H]$^+$.

Step 10

In a 40 mL vial equipped with a stir bar, ((S)-1-((3S,5S)-3-carbamoyl-6-oxo-2,7-diazaspiro[4.4]nonan-2-yl)-4-fluoro-4-methyl-1-oxopentan-2-yl)(methyl)carbamate was treated with HCl (4M/dioxane, 0.67 mL, 20 equiv). The resulting mixture was stirred for 1.5 h and then concentrated to afford (3S,5S)-2-((S)-4-fluoro-4-methyl-2-(methylamino) pentanoyl)-6-oxo-2,7-diazaspiro[4.4]nonane-3-carboxamide hydrochloride as a white solid that was used without purification. ESI MS m/z=329.2 [M+H]$^+$.

Step 11

In a 40 mL vial equipped with a stir bar, (3S,5S)-2-((S)-4-fluoro-4-methyl-2-(methylamino)pentanoyl)-6-oxo-2,7-diazaspiro[4.4]nonane-3-carboxamide hydrochloride (1.0 equiv) prepared in Step 10 was combined with 4,6-difluoro-1H-indole-2-carboxylic acid (26.3 mg, 1.0 equiv) in a mixture of DCM and DMF [DCM (1.11 mL), DMF (0.22 mL), DCM/DMF 5:1, 0.1M]. Next, N-methylmorpholine (47 μL, 3.2 equiv) was added and the mixture was cooled in an ice water bath before the addition of HATU (50.7 mg, 1.0 equiv). The reaction was then slowly warmed to rt and stirred for 14 h. The mixture was diluted with DCM (20 mL) and washed with 1.2M HCl (4 mL) and brine (4 mL) before being passed through a phase separator. Upon concentration, the crude residue was purified by RPHPLC to afford (3S,5S)-2-((S)-2-(4,6-difluoro-N-methyl-1H-indole-2-carboxamido)-4-fluoro-4-methylpentanoyl)-6-oxo-2,7-diazaspiro[4.4]nonane-3-carboxamide (53.2 mg, 79%). ESI MS m/z=508.4 [M+H]$^+$.

Step 12

In a 20 mL vial equipped with a stir bar, (3S,5S)-2-((S)-2-(4,6-difluoro-N-methyl-1H-indole-2-carboxamido)-4-fluoro-4-methylpentanoyl)-6-oxo-2,7-diazaspiro[4.4]nonane-3-carboxamide (53.2 mg, 1.0 equiv) was dissolved in DCM (0.7 mL, 0.15M). The Burgess reagent (50.0 mg, 2.0 equiv) was added and the mixture was stirred for 16 h. The reaction was then diluted with DCM (15 mL), washed once with saturated aqueous sodium bicarbonate (5 mL) and passed through a phase separator. The organic layer was concentrated and the crude residue was purified by RPHPLC to afford N—((S)-1-((3S,5S)-3-cyano-6-oxo-2,7-diazaspiro[4.4]nonan-2-yl)-4-fluoro-4-methyl-1-oxopentan-2-yl)-4,6-difluoro-N-methyl-1H-indole-2-carboxamide as a white solid (26.2 mg, 51% yield). ESI MS m/z=488.2 [M−H]$^−$. $^1$H NMR (400 MHz, acetone-d$_6$, δ ppm): δ 11.20 (s, 1H), 7.16-7.06 (m, 3H), 6.75 (td, J=10.3, 2.1 Hz, 1H), 5.76 (t, J=6.6 Hz, 1H), 4.84 (t, J=8.6 Hz, 1H), 4.26 (d, J=10.5 Hz, 1H), 3.66 (d, J=10.5 Hz, 1H), 3.47 (s, 3H), 3.33-3.18 (m, 2H), 2.55-2.26 (m, 4H), 1.46 (d, J=5.9 Hz, 3H), 1.40 (d, J=6.0 Hz, 3H).

Ex. 2: Synthesis of N—((S)-1-((3S,5S)-3-cyano-6-oxo-2,7-diazaspiro[4.5]decan-2-yl)-4-methyl-1-oxo-pentan-2-yl)-4,6-difluoro-N-methyl-1H-indole-2-carboxamide

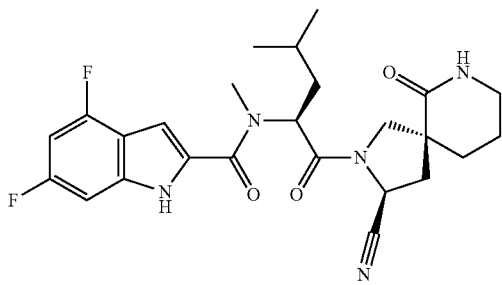 [SMILES: CC(C)C[C@@H](C(=O)N1C[C@]2(CCCNC2=O)C[C@H]1C#N)N(C)C(=O)c1cc2c(F)cc(F)cc2[nH]1]

Step 1
In a 100 mL round bottom flask equipped with a stir bar, 1-(tert-butyl) 4-ethyl 2-methyl (2S,4S)-4-(2-cyanoethyl)pyrrolidine-1,2,4-tricarboxylate (932.8 mg, 1.0 equiv) was dissolved in MeOH (13.2 mL, 0.2M). The solution was then cooled in an ice water bath and cobalt(II) chloride hexahydrate (1.38 g, 2.2 equiv) was added. Sodium borohydride (846 mg, 8.5 equiv) was then added portionwise. The resulting mixture was allowed to warm to room temperature and was stirred for 22 h. The reaction was again cooled in an ice water bath and ammonium hydroxide (6.83 mL, 30 wt %, 20 equiv) was added. After 15 minutes, the reaction mixture was passed through a thick pad of celite using ethyl acetate to rinse. The mixture was concentrated and the crude residue was purified by silica gel column chromatography (gradient elution, 0 to 10% MeOH/DCM) to afford 2-(tert-butyl) 3-methyl (3S,5S)-6-oxo-2,7-diazaspiro[4.5]decane-2,3-dicarboxylate (547.4 mg, 67% yield). ESI MS m/z=313.2 [M+H]$^+$.

Step 2
In a 35 mL high pressure reaction tube, 2-(tert-butyl) 3-methyl (3S,5S)-6-oxo-2,7-diazaspiro[4.5]decane-2,3-dicarboxylate (547.4 mg, 1.0 equiv) was dissolved in methanolic ammonia (7.51 mL, 7M NH$_3$, 30 equiv). The sealed tube was heated at 55° C. for 48 h. The mixture was cooled to rt and additional methanolic ammonia (7.51 mL, 7M NH$_3$, 30 equiv) was added. The sealed tube was heated at 55° C. for an additional 48 h. The mixture was then concentrated, and re-dissolved in methanolic ammonia (15.2 mL, 60 equiv) and heated at 60° C. for 48 h. The mixture was then concentrated, and the crude residue was purified by silica gel column chromatography to afford tert-butyl (3S,5S)-3-carbamoyl-6-oxo-2,7-diazaspiro[4.5]decane-2-carboxylate (335.0 mg). ESI MS m/z=298.2 [M+H]$^+$.

Step 3
In a 40 mL vial equipped with a stir bar, tert-butyl (3S,5S)-3-carbamoyl-6-oxo-2,7-diazaspiro[4.5]decane-2-carboxylate (335.0 mg, 1.0 equiv) was treated with HCl (4M/dioxane, 5.63 mL, 20 equiv). The resulting mixture was stirred for 3 h and then concentrated to afford (3S,5S)-6-oxo-2,7-diazaspiro[4.5]decane-3-carboxamide hydrochloride as a white solid that was used in the next step without further purification. ESI MS m/z=198.0 [M+H].

Step 4
In a 40 mL vial equipped with a stir bar, (3S,5S)-6-oxo-2,7-diazaspiro[4.5]decane-3-carboxamide hydrochloride (263.0 mg, 1.0 equiv) was combined with Boc-N-methyl-L-leucine (276.0 mg, 1.0 equiv) in a mixture of DCM and DMF [DCM (3.60 mL), DMF (0.90 mL), 4:1 DCM/DMF, 0.25M]. The resulting solution was cooled in an ice water bath, and N-methylmorpholine (396 μL, 3.2 equiv) was added. The mixture was stirred until homogenous and HATU (428.0 mg, 1.0 equiv) was added. The reaction was allowed to stir for 3 h while slowly warming to rt. The mixture was then diluted with DCM (20 mL). The organic phase was washed with 1.2M HCl (4.0 mL), saturated aqueous sodium bicarbonate (4.0 mL) and brine (4.0 mL) successively before being passed through a phase separator. Upon concentration, and the crude residue was purified by silica gel column chromatography (gradient elution, 0 to 10% MeOH/DCM) to afford tert-butyl ((S)-1-((3S,5S)-3-carbamoyl-6-oxo-2,7-diazaspiro[4.5]decan-2-yl)-4-methyl-1-oxopentan-2-yl)(methyl)carbamate as a white solid (447.0 mg, 94%). ESI MS m/z=425.2 [M+H]$^+$.

Step 5 In a 40 mL vial equipped with a stir bar, tert-butyl ((S)-1-((3S,5S)-3-carbamoyl-6-oxo-2,7-diazaspiro[4.5]decan-2-yl)-4-methyl-1-oxopentan-2-yl)(methyl)carbamate (447.0 mg, 1.0 equiv) was treated with HCl (4M dioxane, 5.26 mL, 20 equiv). After stirring for 1.5 h, the mixture was concentrated to afford (3S,5S)-2-(methyl-L-leucyl)-6-oxo-2,7-diazaspiro[4.5]decane-3-carboxamide hydrochloride as a white solid that was used in the next step without purification. ESI MS m/z=325.2 [M+H]$^+$.

Step 6
In a 40 mL vial equipped with a stir bar, the (3S,5S)-2-(methyl-L-leucyl)-6-oxo-2,7-diazaspiro[4.5]decane-3-carboxamide hydrochloride (1.0 equiv) prepared in Step 5 was combined with 4,6-difluoro-1H-indole-2-carboxylic acid (208 mg, 1.0 equiv) in a mixture of DCM and DMF [DCM (4.39 mL), DMF (0.88 mL), 5:1 DCM/DMF, 0.2M]. The solution was cooled in an ice water bath and N-methylmorpholine (347 μL, 3.0 equiv) was added. The mixture was stirred until homogenous and HATU (400.0 mg, 1.0 equiv) was added. The reaction was allowed to slowly reach rt and was stirred for 16 h. The mixture was then diluted with DCM (20 mL) and the organic phase was washed with saturated aqueous sodium bicarbonate (7.5 mL) and brine (7.5 mL) before being passed through a phase separator and concentrated. Purification of the residue by silica gel column chromatography (gradient elution, 0 to 15% MeOH/DCM) afforded (3S,5S)-2-(N-(4,6-difluoro-1H-indole-2-carbonyl)-N-methyl-L-leucyl)-6-oxo-2,7-diazaspiro[4.5]decane-3-carboxamide as a white solid (247.6 mg, 47% yield). ESI MS m/z=505.4 [M+H]$^+$.

Step 7
In a 40 mL vial equipped with a stir bar, (3S,5S)-2-(N-(4,6-difluoro-1H-indole-2-carbonyl)-N-methyl-L-leucyl)-6-oxo-2,7-diazaspiro[4.5]decane-3-carboxamide (247.6 mg, 1.0 equiv) was dissolved in DCM (3.28 mL, 0.15M). The Burgess reagent (234 mg, 2.0 equiv) was then added, and the mixture was stirred for 16 h at room temperature. Upon completion, the mixture was diluted with DCM (20 mL) and the organic phase was washed with water (5 mL) and brine (5 mL) before being passed through a phase separator and concentrated. The crude residue was purified by RPHPLC to afford N—((S)-1-((3S,5S)-3-cyano-6-oxo-2,7-diazaspiro[4.5]decan-2-yl)-4-methyl-1-oxopentan-2-yl)-4,6-difluoro-N-methyl-1H-indole-2-carboxamide as a white solid (99.4 mg, 42% yield). ESI MS m/z=484.3 [M−H]⁻. ¹H NMR (400 MHz, acetone-d₆, δ ppm): δ 11.16 (s, 1H), 7.14-7.11 (m, 2H), 6.92 (s, 1H), 6.75 (td, J=10.3, 2.0 Hz, 1H), 5.55-5.52 (m, 1H), 4.81 (t, J=8.5 Hz, 1H), 4.13 (d, J=10.3 Hz, 1H), 3.85 (d, J=10.4 Hz, 1H), 3.45 (s, 3H), 3.33-3.18 (m, 2H), 2.74 (dd, J=13.0, 8.8 Hz, 1H), 2.45 (dd, J=13.0, 8.4 Hz, 1H), 1.94-1.86 (m, 1H), 1.79-1.57 (m, 6H), 1.00 (d, J=6.6 Hz, 3H), 0.98 (d, J=7.0 Hz, 5H).

Ex. 3: Synthesis of N—((S)-1-((3S,5S)-3-cyano-6-oxo-2,7-diazaspiro[4.5]decan-2-yl)-4-fluoro-4-methyl-1-oxopentan-2-yl)-4,6-difluoro-N-methyl-1H-indole-2-carboxamide

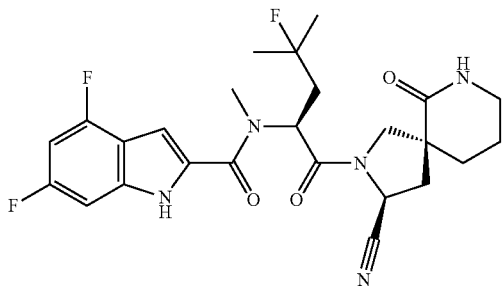 [SMILES: CN(C(=O)c1cc2c(F)cc(F)cc2[nH]1)[C@@H](CC(C)(C)F)C(=O)N1C[C@]2(CCCNC2=O)C[C@H]1C#N]

Ex. 3 was synthesized using a similar protocol to that which was used in the synthesis of Ex. 2. ESI MS m/z=502.2 [M−H]⁻.

Ex. 4: Synthesis of N—((S)-1-((6S,9S)-9-cyano-5-oxo-4,8-diazadispiro[2.2.4⁶.2³]dodecan-8-yl)-4-methyl-1-oxopentan-2-yl)-4,6-difluoro-N-methyl-1H-indole-2-carboxamide

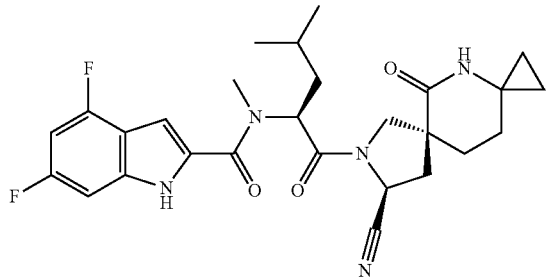 [SMILES: CC(C)C[C@@H](C(=O)N1C[C@]2(CCC3(CC3)NC2=O)C[C@H]1C#N)N(C)C(=O)c1cc2c(F)cc(F)cc2[nH]1]

Step 1

In a flame dried 100 mL round bottom flask equipped with a stir bar, 1-(tert-butyl) 4-ethyl 2-methyl (2S,4S)-4-(2-cyanoethyl)pyrrolidine-1,2,4-tricarboxylate (1.44 g, 1.0 equiv) was dissolved in a mixture of diethyl ether (20.0 mL) and THF (5.0 mL). The resulting solution was cooled to −5° C., and titanium (IV) isopropoxide (1.27 mL, 1.1 equiv) was added. Next, ethylmagnesium bromide (2.71 mL, 2.0 equiv, 3M diethyl ether) was added dropwise over the course of 1 h. Following complete addition of the ethylmagnesium bromide solution, the reaction mixture was warmed to 0° C. After stirring for 40 min at 0° C., boron trifluoride diethyl etherate (1.03 mL, 2.0 equiv) was added. The reaction mixture was allowed to stir for 40 min before being quenched with HCl (6.0 mL, 1.2M) and further diluted with water (50 mL). The aqueous phase was extracted three times with DCM (70 mL) and the combined organic layers were dried over magnesium sulfate. The crude residue was purified by silica gel column chromatography (gradient elution, 0 to 100% ethyl acetate/cyclohexane) to afford 8-(tert-butyl) 9-methyl (6S,9S)-5-oxo-4,8-diazadispiro[2.2.4⁶.2³]dodecane-8,9-dicarboxylate (516.0 mg). ESI MS m/z=339.2 [M+H]⁺.

Step 2

In a 100 mL high pressure reaction tube equipped with a stir bar, 8-(tert-butyl) 9-methyl (6S,9S)-5-oxo-4,8-diazadispiro[2.2.4⁶.2³]dodecane-8,9-dicarboxylate (516.0 mg, 1.0 equiv) was dissolved in methanolic ammonia (7M NH₃, 14.8 mL, 75 equiv). The reaction was heated in the sealed tube for 92.5 h at 60° C. The mixture was then concentrated and the crude residue was purified by silica gel column chromatography (gradient elution, 0 to 15% MeOH/DCM) to afford tert-butyl (6S,9S)-9-carbamoyl-5-oxo-4,8-diazadispiro[2.2.4⁶.2³]dodecane-8-carboxylate (298.8 mg, 67% yield). ESI MS m/z=324.2 [M+H]⁺.

Step 3

In a 40 mL vial equipped with a stir bar, tert-butyl (6S,9S)-9-carbamoyl-5-oxo-4,8-diazadispiro[2.2.4⁶.2³]dodecane-8-carboxylate (298.8 mg, 1.0 equiv) was treated with HCl (4M dioxane, 4.62 mL, 20 equiv). The mixture was stirred for 1.5 h and then concentrated to afford (6S,9S)-5-oxo-4,8-diazadispiro[2.2.4⁶.2³]dodecane-9-carboxamide hydrochloride as a white solid that was used in the subsequent step without purification. ESI MS m/z=224.2 [M+H]⁺.

Step 4

In a 40 mL vial equipped with a stir bar, (6S,9S)-5-oxo-4,8-diazadispiro[2.2.4⁶.2³]dodecane-9-carboxamide hydrochloride (1.0 equiv) prepared in Step 3 was combined with Boc-N-methyl-L-leucine (227.0 mg, 1.0 equiv) in a mixture of DCM and DMF [DCM (3.70 mL), DMF (0.92 mL), 4:1 DCM/DMF, 0.2M]. The resulting suspension was cooled in an ice bath and N-methylmorpholine (325 μL, 3.2 equiv) was added. The mixture was stirred until a homogenous solution was observed, then HATU (351.0 mg, 1.0 equiv) was added and the solution was allowed to slowly reach room temperature. After 5 h, the mixture was diluted with DCM (30 mL) and the organic phase was washed with aqueous HCl (1.2M, 10 mL) and brine (10 mL) before being passed through a phase separator. The crude residue was purified by silica gel column chromatography (gradient elution, 0 to 10% MeOH/DCM) to afford tert-butyl ((S)-1-((6S,9S)-9-carbamoyl-5-oxo-4,8-diazadispiro[2.2.4⁶.2³]dodecan-8-yl)-4-methyl-1-oxopentan-2-yl)(methyl)carbamate (286.2 mg, 69% yield). ESI MS m/z=541.4 [M+H]⁺.

Step 5

In a 40 mL vial equipped with a stir bar, tert-butyl ((S)-1-((6S,9S)-9-carbamoyl-5-oxo-4,8-diazadispiro[2.2.4⁶.2³]dodecan-8-yl)-4-methyl-1-oxopentan-2-yl)(methyl)carbamate (286.2 mg, 1.0 equiv) was treated with HCl (4M dioxane, 3.18 mL, 20 equiv). The resulting mixture was stirred for 1.5 h then concentrated to afford (6S,9S)-8-(methyl-L-leucyl)-5-oxo-4,8-diazadispiro[2.2.4⁶.2³]dodecane-9-carboxamide hydrochloride as a white solid that was used in the subsequent step without purification. ESI MS m/z=351.2 [M+H]⁺.

Step 6

In a 40 mL vial equipped with a stir bar, (6S,9S)-8-(methyl-L-leucyl)-5-oxo-4,8-diazadispiro[2.2.4⁶.2³]dodecane-9-carboxamide hydrochloride (1.0 equiv) was combined with 4,6-difluoro-1H-indole-2-carboxylic acid (125.0 mg, 1.0 equiv) in a mixture of DCM and DMF [DCM (3.53 mL), DMF (0.71 mL), 5:1 DCM/DMF, 0.15M]. The resulting suspension was cooled in an ice water bath and N-methylmorpholine (223 µL, 3.2 equiv) was added. The mixture was stirred until a homogenous solution was observed then HATU (242.0 mg, 1.0 equiv) was added. The reaction mixture was slowly warmed to room temperature and stirred for a 18 h before being diluted with DCM (25 mL). The organic phase was washed with aqueous HCl (10 mL) and brine (10 mL) and then passed through a phase separator. The crude residue was purified by RPHPLC and then by silica gel column chromatography (gradient elution, 0 to 15% McOH/DCM) to afford (6S,9S)-8-(N-(4,6-difluoro-1H-indole-2-carbonyl)-N-methyl-L-leucyl)-5-oxo-4,8-diazadispiro[2.2.4$^6$.2$^3$]dodecane-9-carboxamide as a white solid (156.6 mg, 47% yield). ESI MS m/z=530.4 [M+1]$^+$.

Step 7

In a 40 mL vial equipped with a stir bar, (6S,9S)-8-(N-(4,6-difluoro-1H-indole-2-carbonyl)-N-methyl-L-leucyl)-5-oxo-4,8-diazadispiro[2.2.4$^6$.2$^3$]dodecane-9-carboxamide (156.6 mg) was dissolved in DCM (2.0 mL, 0.15M). The Burgess reagent (141.0 mg, 2.0 equiv) was added and the reaction was stirred for 2 h. At this time, additional Burgess reagent (35.2 mg, 0.5 equiv) was added, and the reaction was stirred for an additional 30 min. The mixture was then diluted with ethyl acetate (50 mL) and saturated aqueous sodium bicarbonate (20 mL). The aqueous phase was extracted with ethyl acetate (30 mL) and the combined organic layers were dried over magnesium sulfate and concentrated. The crude residue was purified by RPHPLC to afford N—((S)-1-((6S,9S)-9-cyano-5-oxo-4,8-diazadispiro[2.2.4$^6$.2$^3$]dodecan-8-yl)-4-methyl-1-oxopentan-2-yl)-4,6-difluoro-N-methyl-1H-indole-2-carboxamide (65.6 mg, 43% yield). ESI MS m/z=510.0 [M–H]$^-$. $^1$H NMR (400 MHz, acetone-d$_6$, δ ppm): δ 12.09 (s, 1H), 7.84 (s, 1H), 7.13-6.99 (m, 2H), 6.90 (td, J=10.4, 2.1 Hz, 1H), 5.38-5.34 (m, 1H), 4.87 (t, J=8.2 Hz, 1H), 3.84-3.76 (m, 2H), 3.27 (s, 3H), 2.55-2.37 (m, 2H), 1.85-1.77 (m, 1H), 1.69-1.50 (m, 6H), 0.96 (d, J=6.4 Hz, 3H), 0.93 (d, J=5.9 Hz, 3H), 0.70-0.63 (m, 2H), 0.57-0.51 (m, 1H), 0.42-0.39 (m, 1H).

Biological Activity

SARS-CoV-2 3C-like (3CL) protease fluorescence assay (FRET): Recombinant SARS-CoV-2 3CL-protease was expressed and purified. TAMRA-SITSAVLQSGFRKMK-Dabcyl-OH peptide 3CLpro substrate was synthesized. Black, low volume, round-bottom, 384 well microplates were used. In a typical assay, 0.85 µL of test compound was dissolved in DMSO then incubated with SARS-CoV-2 3CL-protease (10 nM) in 10 µL assay buffer (50 mM HEPES [pH 7.5], 1 mM DTT, 0.01% BSA, 0.01% Triton-X 100) for 30 min at RT. Next, 10 µL of 3CL-protease substrate (40 µM) in assay buffer was added and the assays were monitored continuously for 1 h in an Envision multimode plate reader operating in fluorescence kinetics mode with excitation at 540 nm and emission at 580 nm at RT. No compound (DMSO only) and no enzyme controls were routinely included in each plate. All experiments were run in duplicate. Data Analysis: SARS-CoV-2 3CL-protease enzyme activity was measured as initial velocity of the linear phase (RFU/s) and normalized to controlled samples DMSO (100% activity) and no enzyme (0% activity) to determine percent residual activity at various concentrations of test compounds (0-10 µM). Data were fitted to normalized activity (variable slope) versus concentration fit in GraphPad Prism 7 to determine IC$_{50}$. All experiments were run in duplicate, and IC$_{50}$ ranges are reported as follows: A<0.1 µM; B 0.1-1 µM; C>1 µM.

TABLE 1

Summary of Activities

| Compound | FRET IC$_{50}$ | Compound | FRET IC$_{50}$ |
|---|---|---|---|
| 1 | A | 2 | A |
| 3 | A | 4 | A |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I):

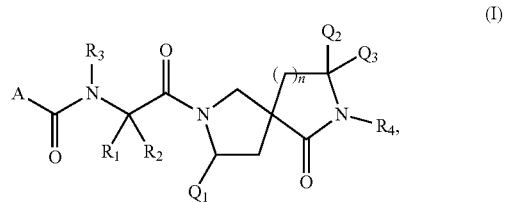

or a pharmaceutically acceptable salt thereof, wherein:

A is selected from:
 1) —R$_{11}$;
 2) —OR$_{12}$;
 3) —NR$_{17}$R$_{18}$; and
 4) —C(R$_{13}$R$_{14}$)N(R$_{17}$R$_{18}$);

n is 1, 2, or 3;

Q$_1$ is selected from:
 1) —CN;
 2) —C(O)R$_{15}$;
 3) —CH(OH)SO$_3$R$_{16}$;
 4) —C(O)NR$_{13}$R$_{14}$;
 5) —C(O)C(O)NR$_{13}$R$_{14}$; and
 6) Optionally substituted —C$_2$-C$_8$ alkynyl;

R$_1$, R$_2$, R$_3$, Q$_2$, and Q$_3$ are each independently selected from:
 1) Hydrogen;
 2) Optionally substituted —C$_1$-C$_8$ alkyl;
 3) Optionally substituted —C$_2$-C$_8$ alkenyl;
 4) Optionally substituted —C$_2$-C$_8$ alkynyl;
 5) Optionally substituted —C$_3$-C$_8$ cycloalkyl;
 6) Optionally substituted 3- to 8-membered heterocycloalkyl;
 7) Optionally substituted aryl;
 8) Optionally substituted arylalkyl;
 9) Optionally substituted heteroaryl; and
 10) Optionally substituted heteroarylalkyl;

alternatively, R$_1$ and R$_2$ are taken together with the carbon atom to which they are attached to form an optionally substituted 3- to 8-membered carbocyclic ring or an optionally substituted 3- to 8-membered heterocyclic ring;

alternatively, Q$_2$ and Q$_3$ are taken together with the carbon atom to which they are attached to form an optionally substituted 3- to 8-membered carbocyclic ring or an optionally substituted 3- to 8-membered heterocyclic ring;

R₄ is hydrogen, optionally substituted —C₁-C₄ alkyl, optionally substituted C₂-C₄-alkenyl, or optionally substituted —C₃-C₆ cycloalkyl;

R₁₁ and R₁₂ are each independently selected from:
1) Optionally substituted —C₁-C₈ alkyl;
2) Optionally substituted —C₂-C₈ alkenyl;
3) Optionally substituted —C₂-C₈ alkynyl;
4) Optionally substituted —C₃-C₈ cycloalkyl;
5) Optionally substituted 3- to 8-membered heterocycloalkyl;
6) Optionally substituted aryl;
7) Optionally substituted arylalkyl;
8) Optionally substituted heteroaryl; and
9) Optionally substituted heteroarylalkyl;

R₁₃, R₁₄, and R₁₇ each independently selected from:
1) Hydrogen;
2) Optionally substituted —C₁-C₈ alkyl;
3) Optionally substituted —C₂-C₈ alkenyl;
4) Optionally substituted —C₂-C₈ alkynyl;
5) Optionally substituted —C₃-C₈ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;
alternatively, R₁₃ and R₁₄ are taken together with the carbon atom to which they are attached to form an optionally substituted 3- to 8-memberedheterocyclic ring;

R₁₅ is hydrogen, hydroxy, or optionally substituted —C₁-C₈ alkyl;

R₁₆ is hydrogen or Na³⁰; and

R₁₈ is selected from:
—C(O)R₁₁;
—C(O)OR₁₁;
—C(O)NR₁₃R₁₄;
—S(O)₂R₁₁;
Hydrogen;
Optionally substituted —C₁-C₈ alkyl;
Optionally substituted —C₂-C₈ alkenyl;
Optionally substituted —C₂-C₈ alkynyl;
Optionally substituted —C₃-C₈ cycloalkyl;
Optionally substituted 3- to 8-membered heterocycloalkyl;
Optionally substituted aryl;
Optionally substituted arylalkyl;
Optionally substituted heteroaryl; and
Optionally substituted heteroarylalkyl.

2. The compound of claim 1, wherein Q₁ is —CN, and R₄ is hydrogen.

3. The compound of claim 1, wherein A is derived from one of the following by removal of a hydrogen atom and is optionally substituted:

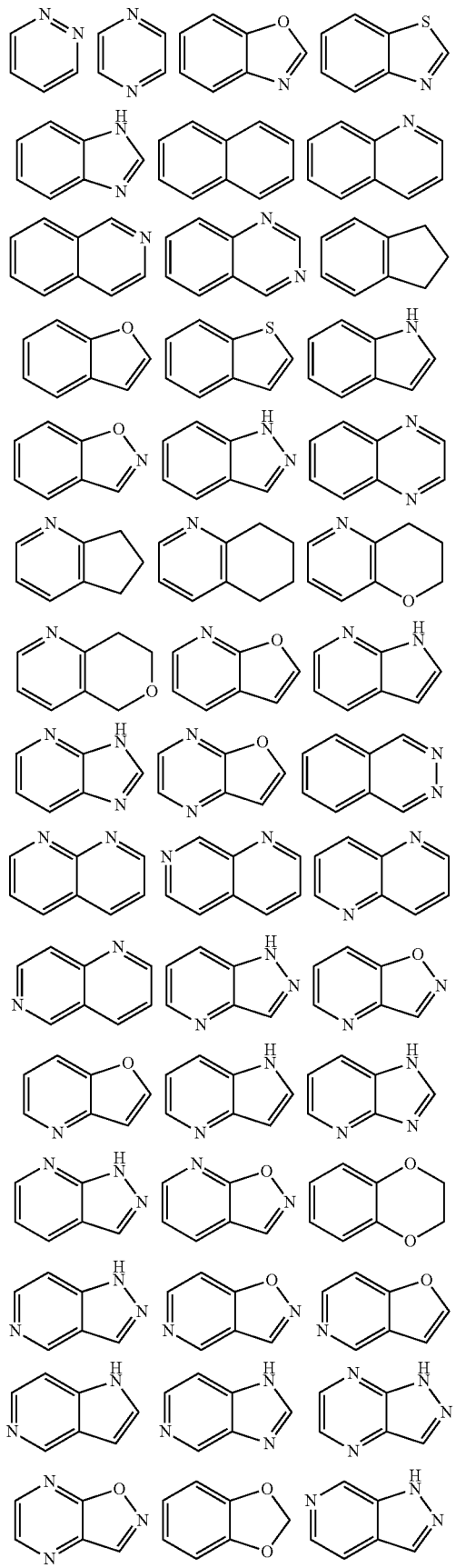

-continued

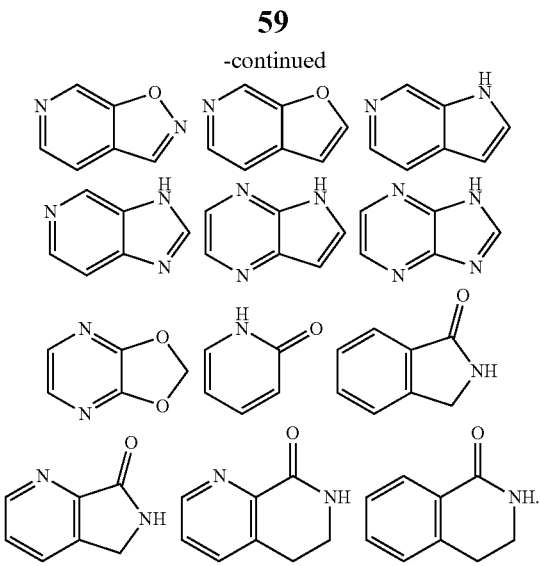

4. The compound of claim 1 represented by Formulae (IV-1) or Formula (IV-2), or a pharmaceutically acceptable salt thereof:

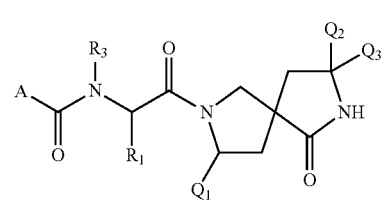
(IV-1)

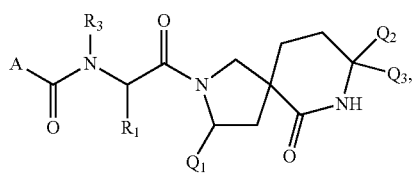
(IV-2)

wherein A, $Q_1$, $Q_2$, $Q_3$, $R_1$, and $R_3$ are as defined in claim 1.

5. The compound of claim 1, represented by one of Formulae (VII-1) to (VII-9), or a pharmaceutically acceptable salt thereof:

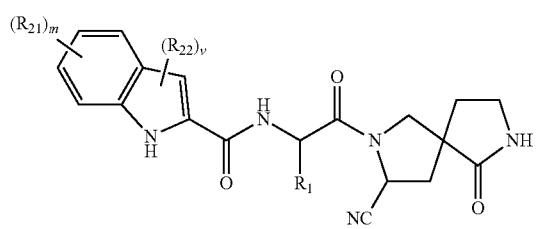
(VII-1)

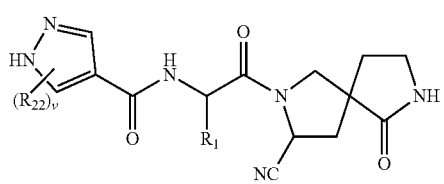
(VII-2)

-continued

(VII-3)

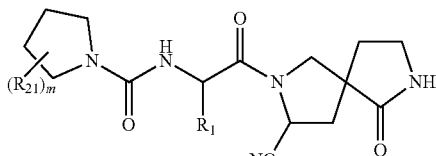
(VII-4)

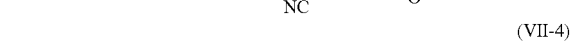
(VII-5)

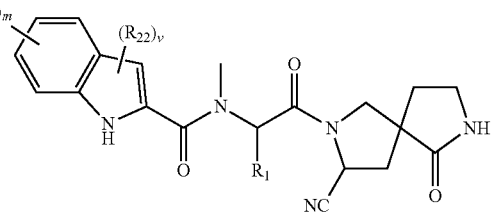
(VII-6)

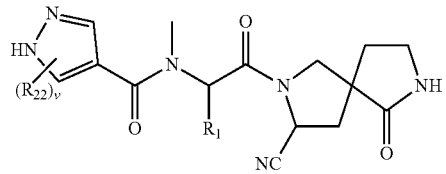
(VII-7)

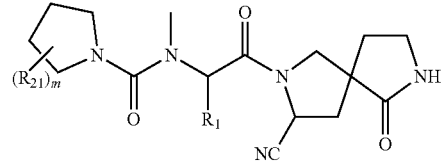
(VII-8)

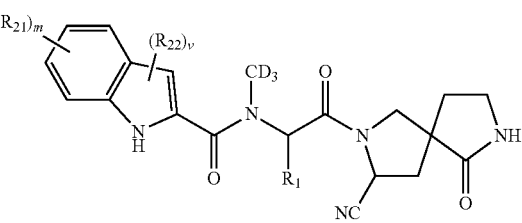
(VII-9)

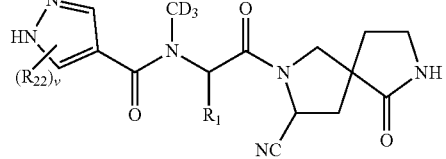

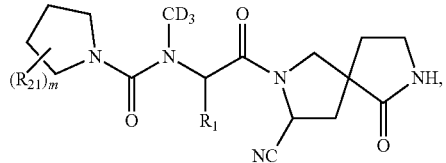

wherein each $R_{21}$ and $R_{22}$ are independently selected from:
1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$alkyl;
8) Optionally substituted —$C_3$-$C_8$cycloalkyl;

9) Optionally substituted 3- to 8-membered heterocycloalkyl;

10) Optionally substituted aryl; and

11) Optionally substituted heteroaryl;

m is 0, 1, 2, 3, or 4; v is 0, 1, or 2, and $R_1$, $R_{13}$, and $R_{14}$ are as defined in claim 1.

6. The compound of claim 1, represented by one of Formulae (VIII-1) to (VIII-9), or a pharmaceutically acceptable salt thereof:

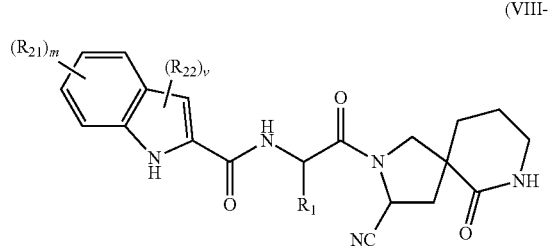
(VIII-1)

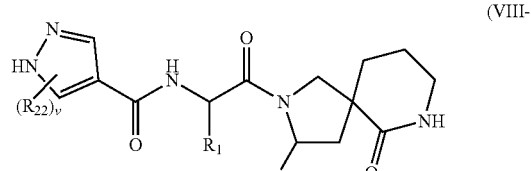
(VIII-2)

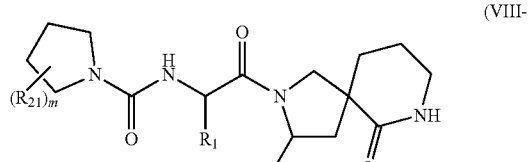
(VIII-3)

(VIII-4)

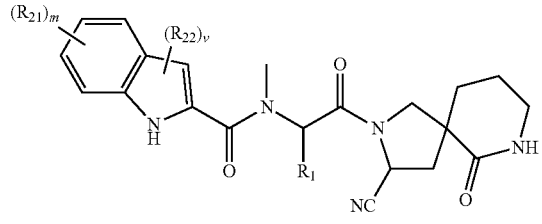
(VIII-5)

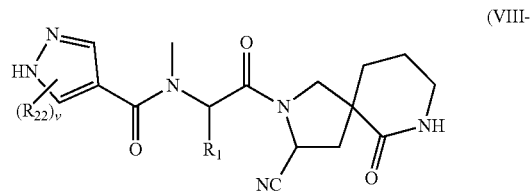
(VIII-6)

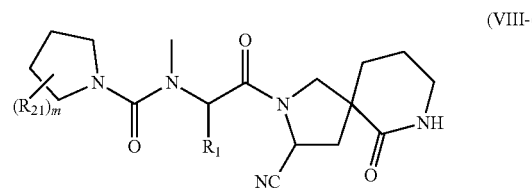

-continued

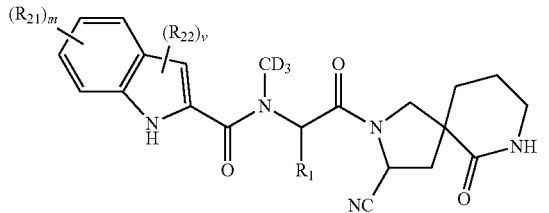
(VIII-7)

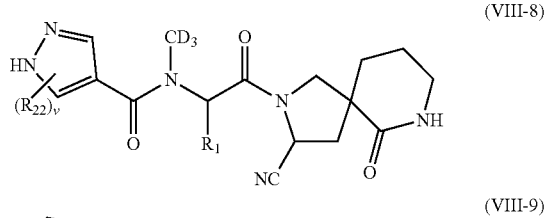
(VIII-8)

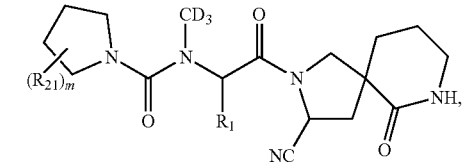
(VIII-9)

wherein each $R_{21}$ and $R_{22}$ is independently selected from:

1) Halogen;
2) —CN;
3) —OR$_{13}$;
4) —SR$_{13}$;
5) —NR$_{13}$R$_{14}$;
6) —OC(O)NR$_{13}$R$_{14}$;
7) Optionally substituted —C$_1$-C$_6$ alkyl;
8) Optionally substituted —C$_3$-C$_8$ cycloalkyl;
9) Optionally substituted 3- to 8-membered heterocycloalkyl;
10) Optionally substituted aryl; and
11) Optionally substituted heteroaryl;

m is 0, 1, 2, 3, or 4; v is 0, 1, or 2, and $R_1$, $R_{13}$, and $R_{14}$ are as defined in claim 1.

7. The compound of claim 1, represented by Formula (X), or a pharmaceutically acceptable salt thereof:

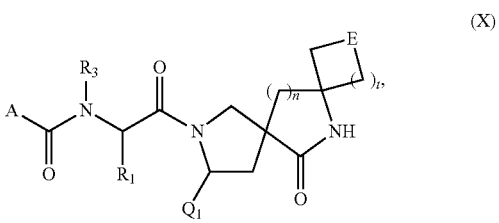
(X)

wherein E is —C(R$_{13}$R$_{14}$)—, —N(R$_{13}$)—, or —O—, t is 0, 1, 2, 3, or 4, and n, A, Q$_1$, R$_{13}$, R$_{14}$, R$_1$, and R$_3$ as defined in claim 1.

8. The compound of claim 1, selected from the compounds set forth below or a pharmaceutically acceptable salt thereof:

| Compound | Structure |
|---|---|
| 1 | 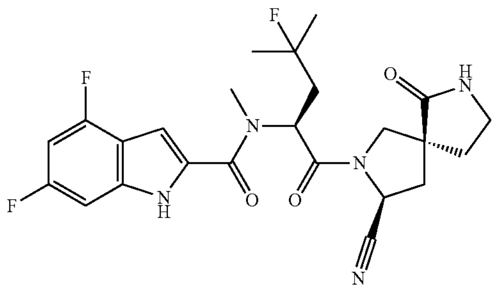 [SMILES: CN(C(=O)c1cc2c(F)cc(F)cc2[nH]1)[C@@H](CC(C)(C)F)C(=O)N1C[C@]2(CCNC2=O)C[C@H]1C#N] |
| 2 | 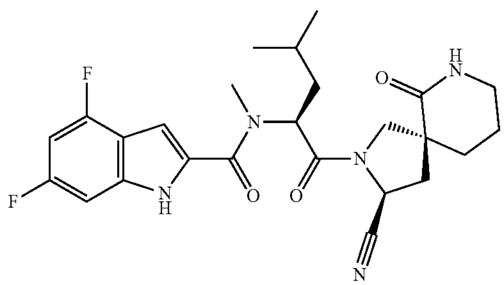 [SMILES: CC(C)C[C@@H](C(=O)N1C[C@]2(CCCNC2=O)C[C@H]1C#N)N(C)C(=O)c1cc2c(F)cc(F)cc2[nH]1] |
| 3 | 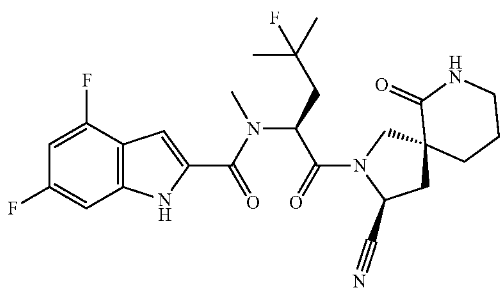 [SMILES: CN(C(=O)c1cc2c(F)cc(F)cc2[nH]1)[C@@H](CC(C)(C)F)C(=O)N1C[C@]2(CCCNC2=O)C[C@H]1C#N] |
| 4 | 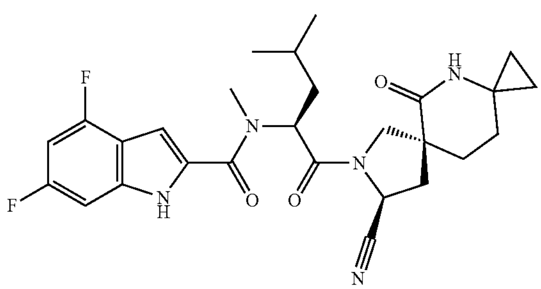 |

9. A pharmaceutical composition comprising a compound according to claim 1 and a pharmaceutically acceptable carrier or excipient.

10. A method of treating or preventing a virus infection in a subject susceptible to or suffering from the virus infection, the method comprising administering to the subject an effective amount of a compound according to claim 1.

11. A method of treating or preventing a coronavirus infection in a subject in need thereof, comprising administering to the subject a therapeutically effective amount of a compound or a combination of compounds according to claim 1.

12. The method according to claim 11, wherein the coronavirus is a 229E, NL63, OC43, HKU1, SARS-CoV-1, SARS-CoV-2 or a MERS coronavirus.

13. A method of inhibiting viral 3C protease or viral 3CL protease in a subject, comprising administering to said subject an effective amount of a compound according to claim 1, or a pharmaceutically acceptable salt thereof.

14. The method according to claim 13, wherein the subject is a human.

15. A method of treating a respiratory disorder in a subject in need thereof, comprising administering to the subject an effective amount of a compound of claim 1.

16. The method according to claim 15, wherein the compound or pharmaceutical composition is administered orally, subcutaneously, intravenously or by inhalation.

* * * * *

UNITED STATES PATENT AND TRADEMARK OFFICE
CERTIFICATE OF CORRECTION

PATENT NO. : 11,993,600 B2
APPLICATION NO. : 18/075567
DATED : May 28, 2024
INVENTOR(S) : Joseph D. Panarese et al.

It is certified that error appears in the above-identified patent and that said Letters Patent is hereby corrected as shown below:

In the Claims

At Column 57
In Claim 1, Line 27 delete "carbon" and insert -- nitrogen --; and
In Claim 1, Line 32 delete "$Na^{30}$" and insert -- $Na^+$ --.

At Column 59
In Claim 4, Line 21 delete "Formulae" and insert -- Formula --.

At Column 62
In Claim 7, Line 62 before "$R_3$" insert -- are --.

Signed and Sealed this
Second Day of July, 2024

Katherine Kelly Vidal
*Director of the United States Patent and Trademark Office*